(12) United States Patent
French et al.

(10) Patent No.: US 8,579,915 B2
(45) Date of Patent: Nov. 12, 2013

(54) SYSTEMS, METHODS AND DEVICES FOR REMOVING OBSTRUCTIONS FROM A BLOOD VESSEL

(75) Inventors: Ron French, Santa Clara, CA (US); Scott Wilson, Redwood City, CA (US); Neil Barman, Menlo Park, CA (US); Emily Vu, San Jose, CA (US); John Miller, Redwood City, CA (US)

(73) Assignee: Concentric Medical, Inc., Mountain View, CA (US)

( * ) Notice: Subject to any disclaimer, the term of this patent is extended or adjusted under 35 U.S.C. 154(b) by 0 days.

(21) Appl. No.: 13/352,312

(22) Filed: Jan. 17, 2012

(65) Prior Publication Data

US 2012/0143231 A1 Jun. 7, 2012

Related U.S. Application Data

(63) Continuation of application No. 11/655,779, filed on Jan. 18, 2007, now abandoned.

(51) Int. Cl.
*A61B 17/22* (2006.01)

(52) U.S. Cl.
USPC .......................................... 606/127; 606/159

(58) Field of Classification Search
CPC ..................... A61B 17/221; A61B 2017/2212; A61B 17/2217
USPC ......... 606/113, 200, 159, 114, 127, 198, 194, 606/195
See application file for complete search history.

(56) References Cited

U.S. PATENT DOCUMENTS

| 4,994,069 | A | * | 2/1991 | Ritchart et al. | 606/191 |
|---|---|---|---|---|---|
| 5,304,194 | A | * | 4/1994 | Chee et al. | 606/191 |
| 6,350,271 | B1 | * | 2/2002 | Kurz et al. | 606/159 |
| 2002/0193827 | A1 | * | 12/2002 | McGuckin et al. | 606/200 |
| 2003/0191492 | A1 | * | 10/2003 | Gellman et al. | 606/200 |
| 2004/0116959 | A1 | * | 6/2004 | McGuckin et al. | 606/200 |

* cited by examiner

*Primary Examiner* — Darwin Erezo
*Assistant Examiner* — Shaun L David
(74) *Attorney, Agent, or Firm* — Jens E. Hoekendijk

(57) ABSTRACT

The present invention provides an obstruction removing device and a method for making the obstruction removing device. The method includes two mandrels with an elongate element being wound around the first mandrel and then wrapped around the second mandrel. The mandrels are movable relative to one another so that the second mandrel may be moved closer to the first mandrel after winding the element around the first mandrel and before winding the element around the second mandrel.

8 Claims, 45 Drawing Sheets

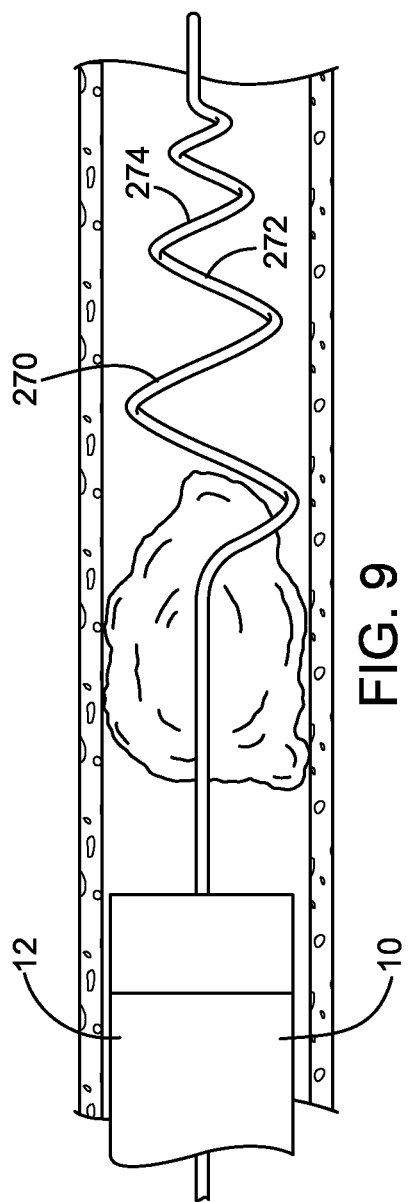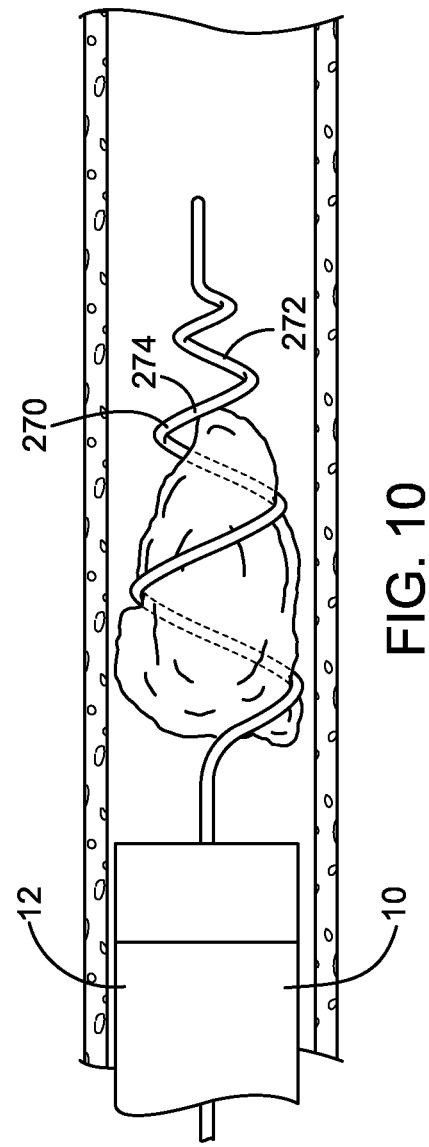

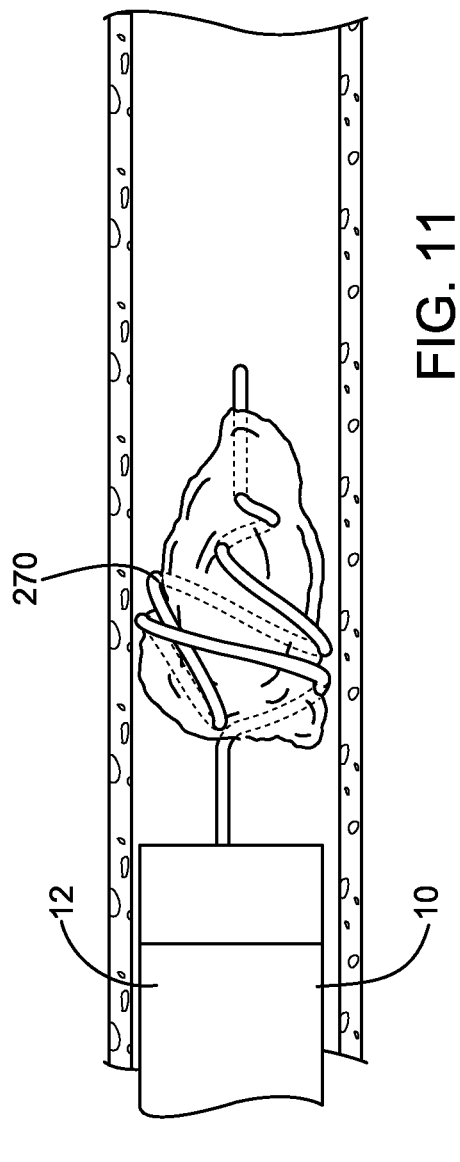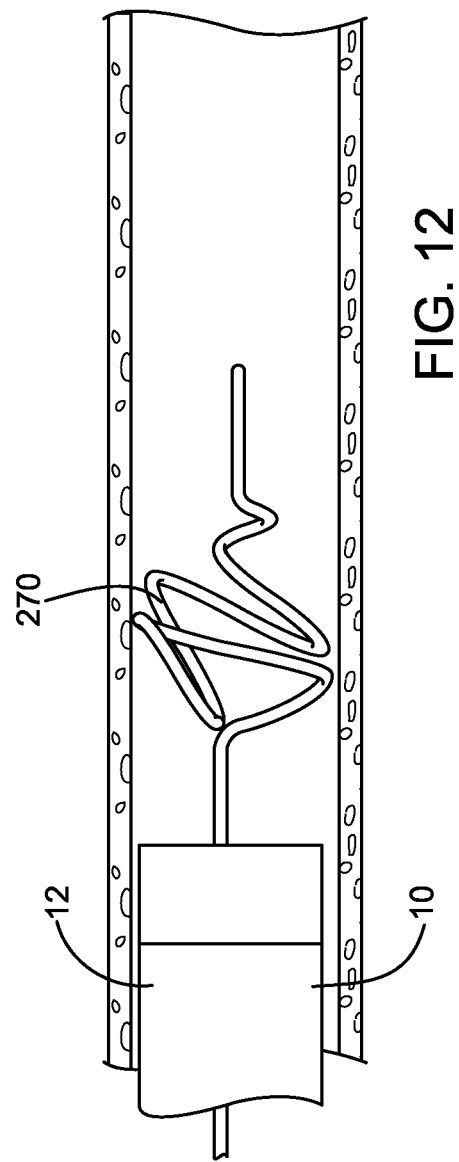

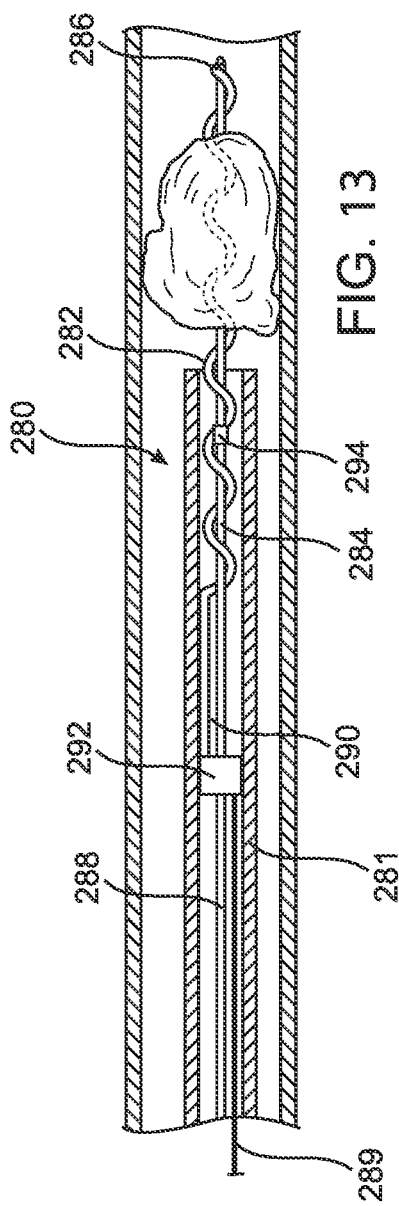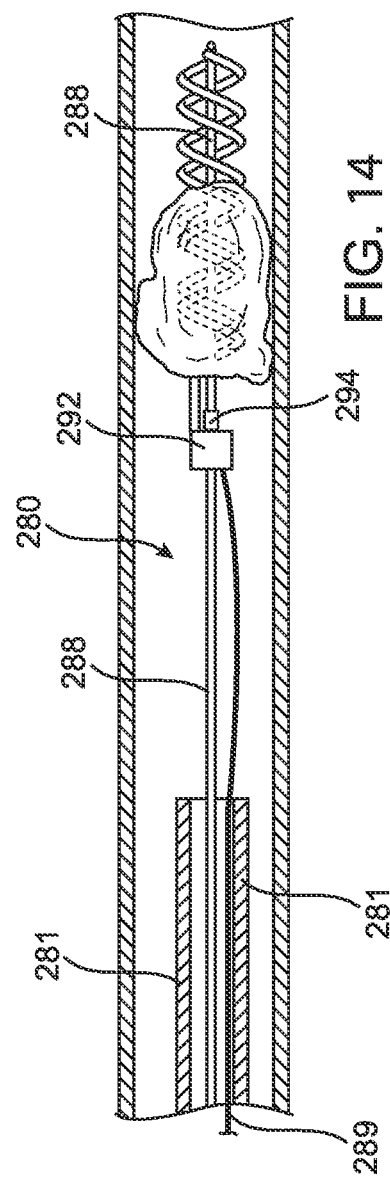

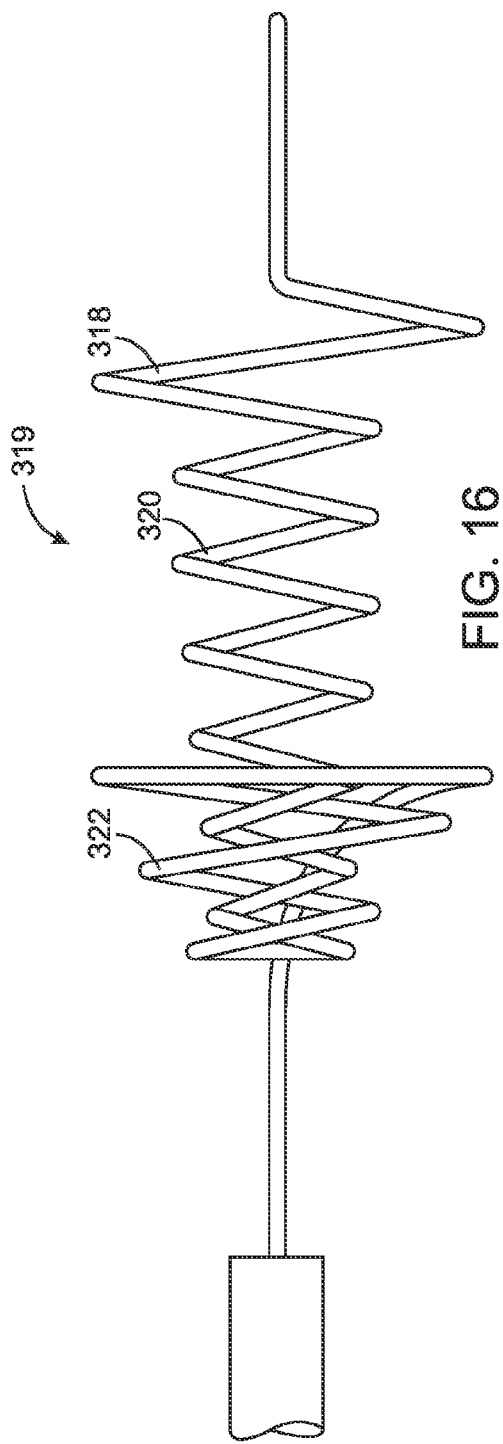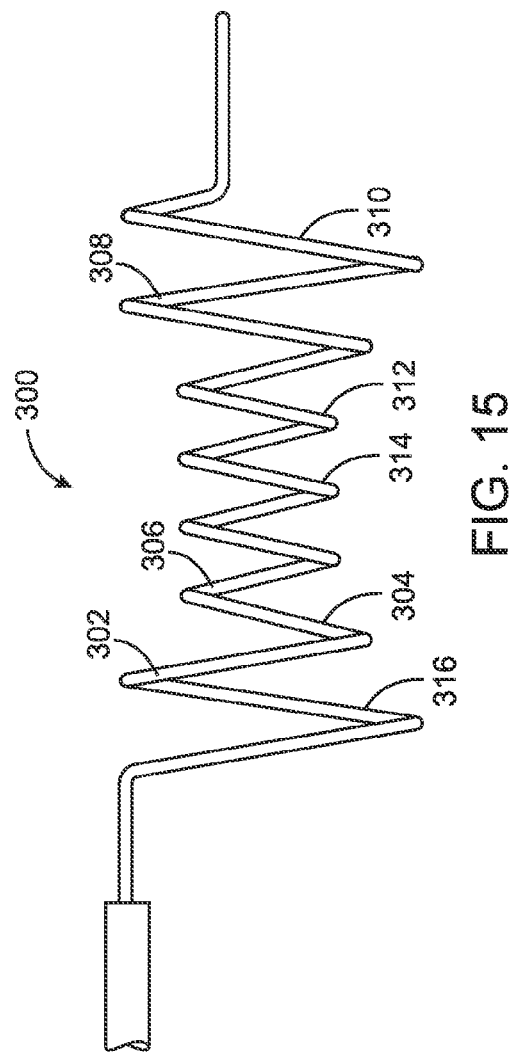

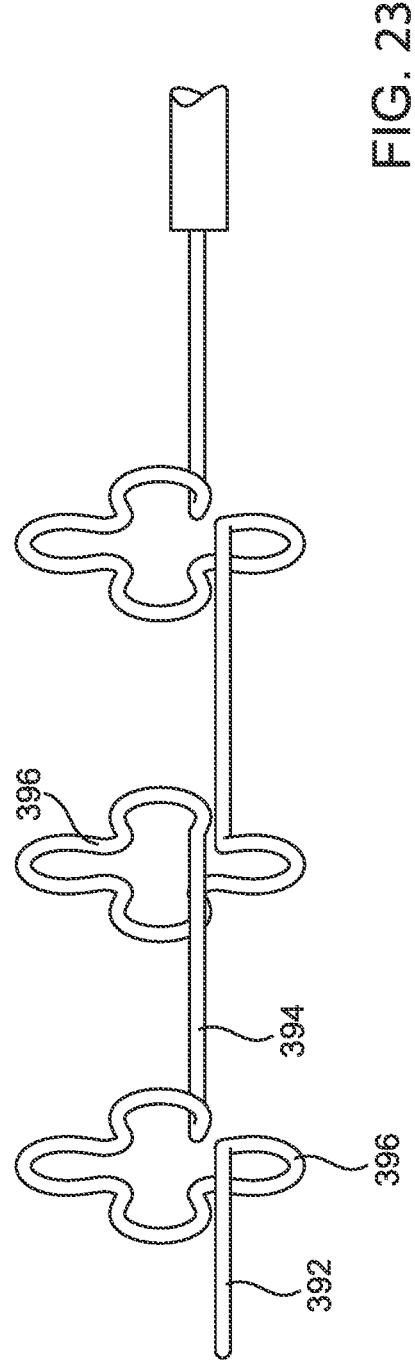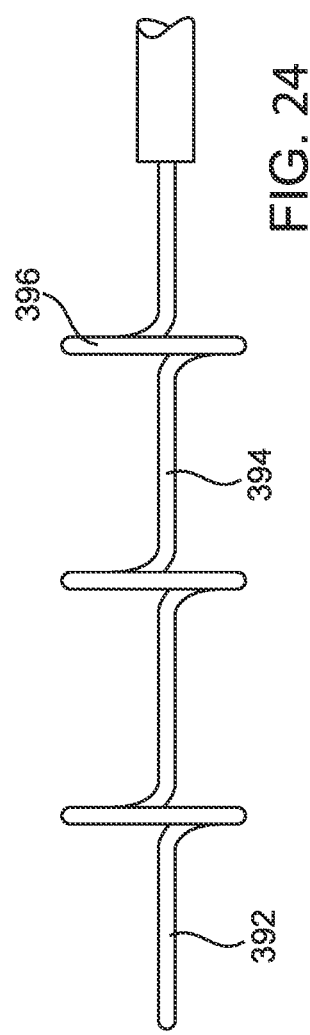

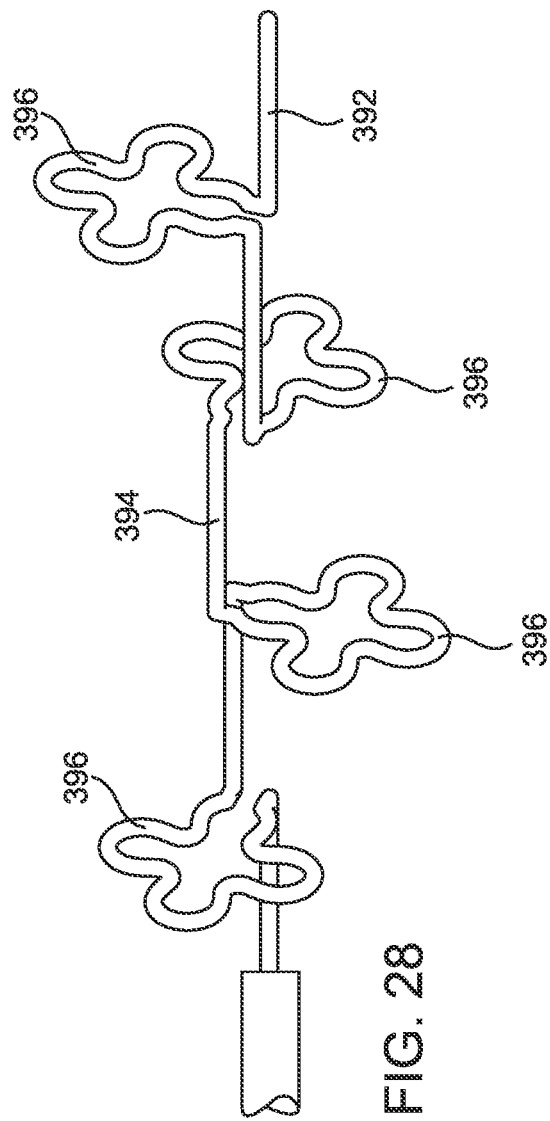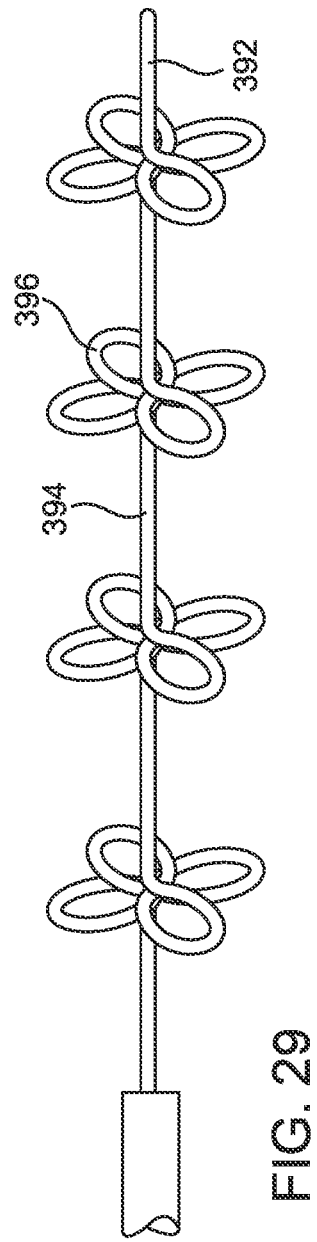

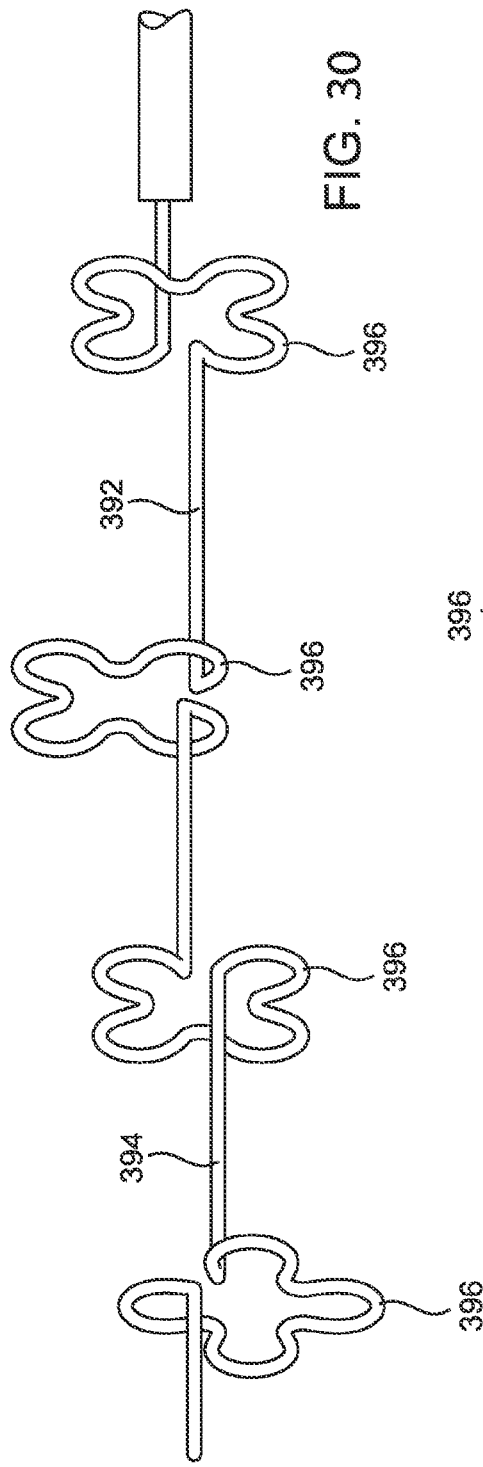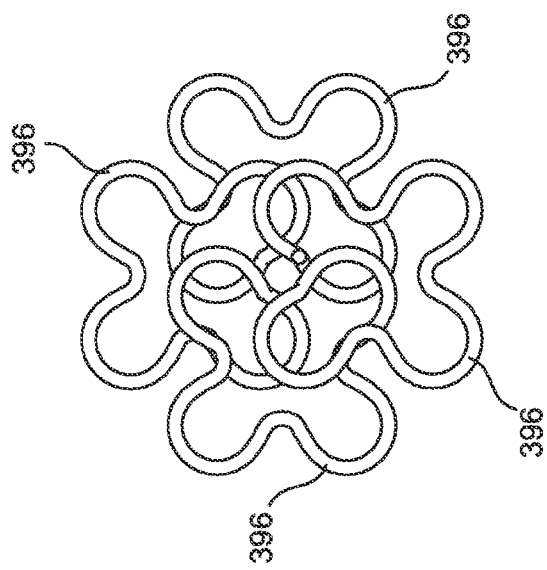

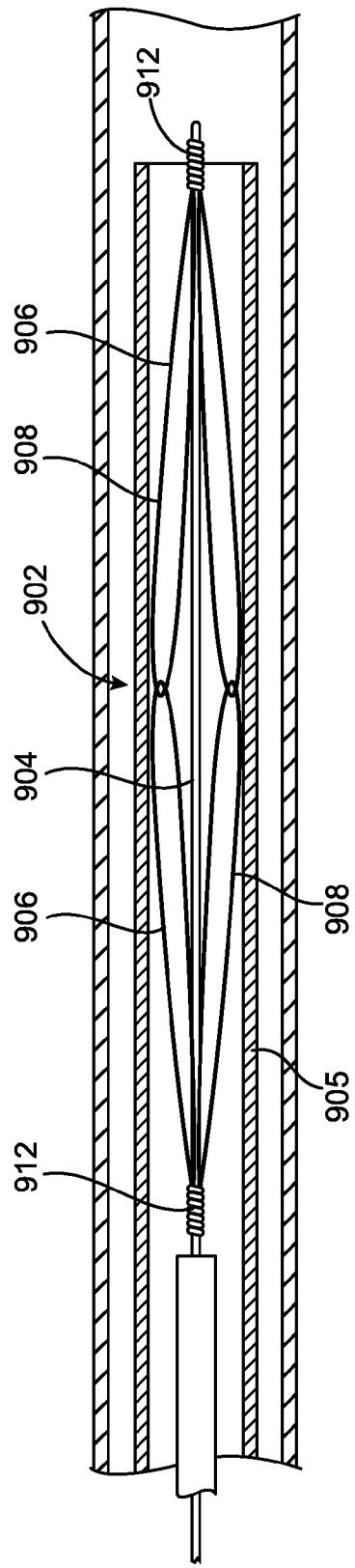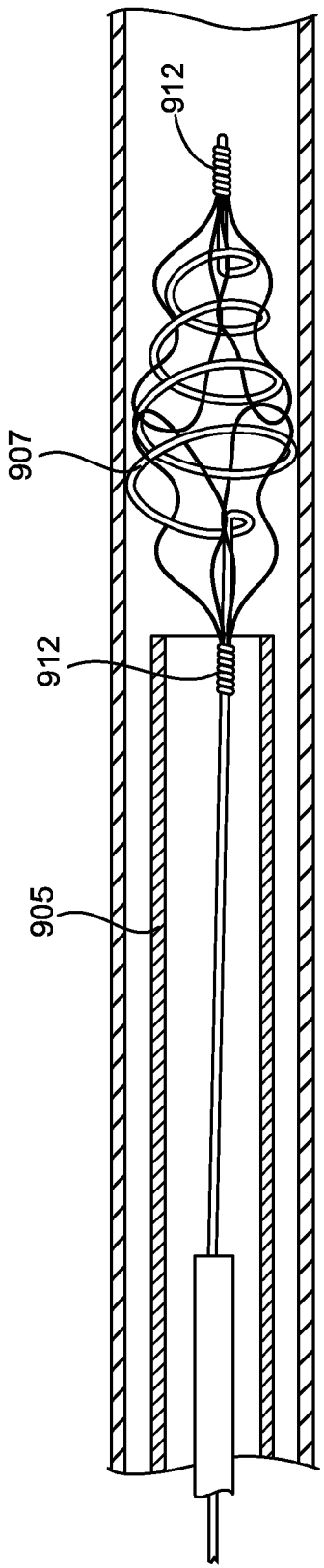

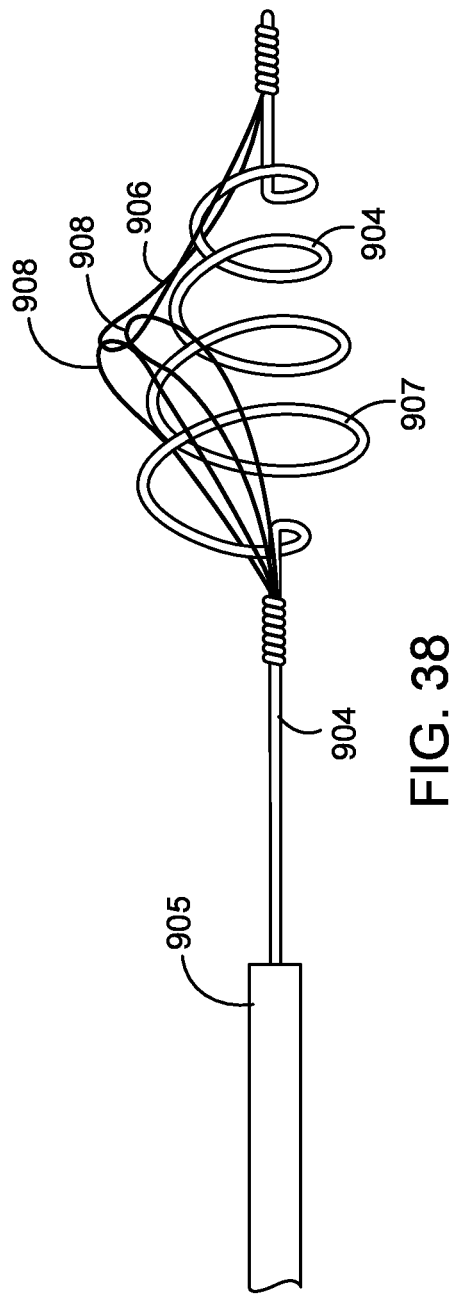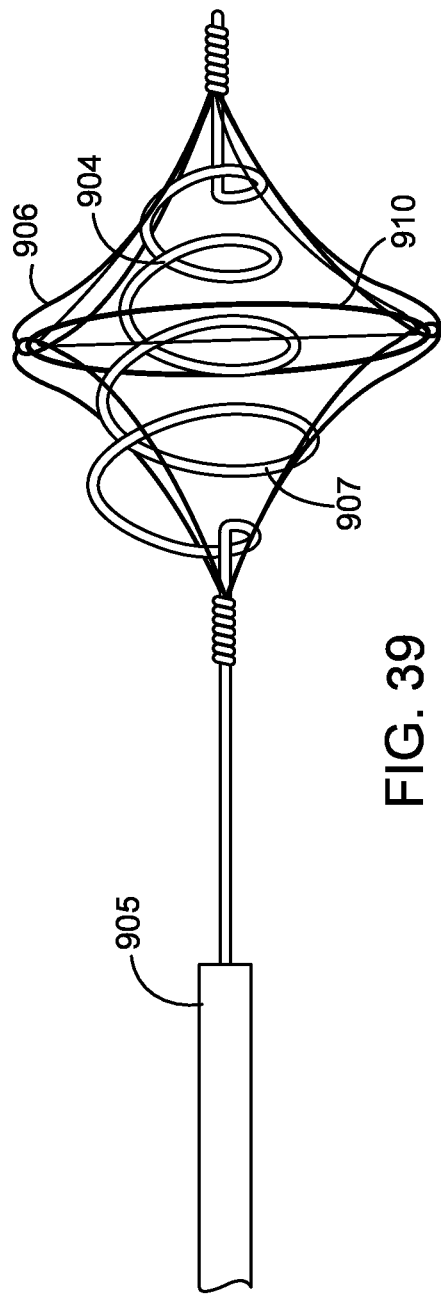

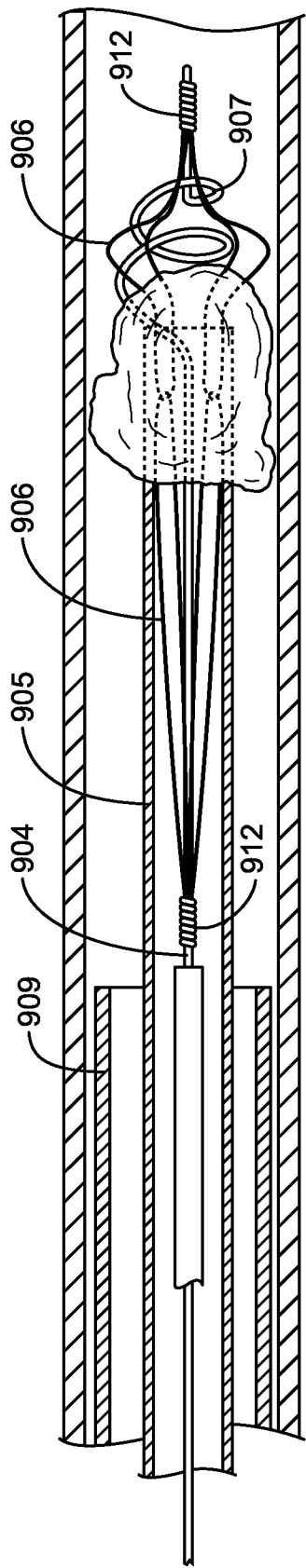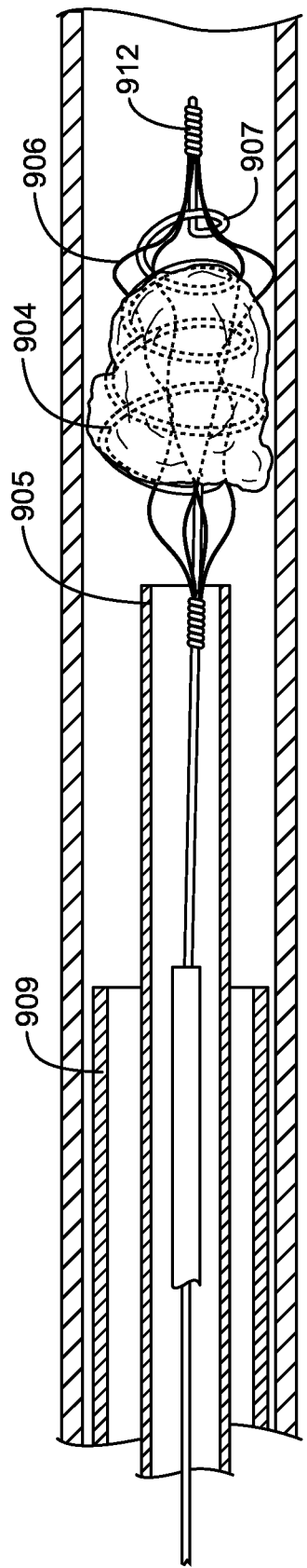
FIG. 44
FIG. 45

SYSTEMS, METHODS AND DEVICES FOR REMOVING OBSTRUCTIONS FROM A BLOOD VESSEL

CROSS-REFERENCE TO RELATED APPLICATIONS

This application is a continuation of U.S. application Ser. No. 11/655,779, filed Jan. 18, 2007 (now abandoned), the full disclosure of which is hereby incorporated by reference.

BACKGROUND OF THE INVENTION

1. Field of the Invention

The present invention is also directed to methods and devices for removing obstructions from blood vessels. The device may be used to retrieve and remove clots and other biological obstructions or to retrieve embolic coils and the like which have been misplaced or have migrated to an undesirable location.

Obstruction removal devices are disclosed in U.S. Pat. Nos. 5,895,398 and 6,824,545, which are hereby incorporated by reference.

The present invention is directed to methods and devices for removing obstructions from blood vessels. The device may be used to retrieve and remove clots and other biological obstructions. The device may also be used to retrieve embolic coils and the like which have been misplaced or have migrated to an undesirable location.

One such obstruction removal device is disclosed in U.S. Pat. No. 5,895,398 which is hereby incorporated by reference. The device has an expandable engaging member which is introduced into the blood vessel to engage the obstruction for removal.

The present invention is also directed to devices, systems and methods which use an expandable capture element when removing obstructions from a blood vessel. One such system for removing obstructions in a blood vessel is described in U.S. Pat. No. 5,102,415 to Guenther et al. The system described in U.S. Pat. No. 5,102,415 has a balloon catheter and a catheter having an expandable tip which receives the obstruction. The balloon catheter is passed through the obstruction while the balloon is deflated. The balloon is then inflated and the tip of the catheter is expanded. The balloon is then moved proximally so that the obstruction is pulled into the expanded tip of the catheter. A problem with the system of U.S. Pat. No. 5,102,415 is that the interaction between the balloon catheter and the leading edge of the catheter may tend to shear off portions of the obstruction. This can cause obvious problems when working in sensitive vascular areas.

The present invention is directed to additional devices and methods for removing obstructions in a blood vessel.

SUMMARY OF THE INVENTION

In a first aspect of the present invention, a method of forming an obstruction removing element is also described. The method includes use of a two part mandrel with at least one of the mandrels being movable relative to the other mandrel. An elongate element is wrapped around the first mandrel and then the second mandrel is moved to a position closer to the first mandrel. The elongate element is then wrapped around the second mandrel to complete the desired shape. The elongate element may be wrapped over an end of the first mandrel so that the elongate element extends over an apex of the first mandrel and intersects the longitudinal axis of the first mandrel.

In another aspect of the present invention, a device and method for removing an obstruction are described. The obstruction removing device has at least two loops defining a longitudinal axis at a proximal section or distal section or both. An intermediate section has two crossing portions which intersect the longitudinal axis. The device is introduced into a patient and then used to engage and remove the obstruction.

In accordance with the present invention, device and methods for removing obstructions are also provided. In a first aspect of the invention, an obstruction removal device is provided which has an obstruction engaging element extending from an insertion element. The engaging element is movable from a collapsed position to an expanded position. The engaging element forms coils having varying diameter wherein the coils at a distal portion are larger than coils at an intermediate portion. The distal portion forms a relatively closed structure which prevents the obstruction, or any part thereof, from migrating downstream. The distal portion is expanded distal to the obstruction while the proximal portion engages and holds the obstruction.

In another aspect of the present invention, another obstruction removal device is provided which has at least one closed loop and preferably two closed loops. The closed loop provides an advantage when advanced through a catheter or sheath in that the closed loop produces opposing radial forces on the catheter or sheath through which the loop is advanced. In this manner, the obstruction removal device can be advanced more easily through the catheter or sheath to prevent binding or kinking of the device during advancement. In a preferred embodiment, the obstruction removal device has two loops of varying diameter with the distal loop having a larger diameter. Each of the loops lie in a plane with the planes of the two loops preferably being perpendicular to one another.

In another aspect of the invention, another obstruction removal device is provided which has wound sections formed by one or more filaments which are separated by sections substantially free of the filaments. The intermittent wound sections provide discrete portions where the obstruction can be engaged. In an embodiment, the wound sections can slide on the core element to provide flexibility when advancing the obstruction removal device. The wound sections and sections free of filament are preferably about 1-5 mm long. The obstruction removal device preferably has at least three wound sections and more preferably at least five wound sections.

In still another aspect of the invention, another obstruction removal device is provided which has alternating large and small diameter portions. In a preferred embodiment, the obstruction removal device has at least four large diameter sections and three smaller diameter portions. The alternating large and small diameter portions may help to engage certain types of obstructions and can also help to prevent parts of the obstruction from breaking off and migrating downstream.

Any of the obstruction removal devices described herein may also be used with a source of power coupled to the obstruction removal device for use as described below. The source of power may simply produce a positive or negative charge or may be an RF energy source. The source of power may be used to help the obstruction removal device penetrate and engage the obstruction and may also be used to adhere the obstruction to the obstruction removal device as will be described. In a preferred embodiment, a negative charge is provided when advancing the obstruction removal device into the obstruction and a positive charge, or RF energy, is supplied to adhere the device to the obstruction.

The devices of the present invention may be manufactured in any suitable manner. In another aspect of the present invention, the obstruction removal device has a core element surrounded by a sheath. A strand, preferably about four strands, are positioned between the core element and the tube. The strand and the tube prevent any part of the obstruction removal device from breaking free should the core element fail. The strand and tube will hold the obstruction removal device together even if the core element breaks. The sheath is preferably flexible so that the sheath can undergo much larger deflections than the core element.

The obstruction removal devices of the present invention may also be advanced through a guide catheter having a flow restricting element which is preferably a balloon but may be any other suitable structure. The flow restricting element is expanded to reduce blood flow through the obstructed vessel to minimize the likelihood that the obstruction will migrate downstream.

In another aspect of the invention, a system is provided which has an expandable capture element and an obstruction engaging device which together work to remove an obstruction from a blood vessel. The capture element is advanced through the patient in a collapsed position and is expanded when at the desired location. The obstruction engaging device preferably has one or more filaments which provide a relatively flexible interaction between the engaging device and the capture element. This provides advantages over the use of a balloon catheter as described in greater detail below. The obstruction engaging device preferably has 1-4 filaments and more preferably 1-2 filaments. Of course, the obstruction engaging device may have more filaments without departing from various aspects of the invention and, in fact, the device may form a filter which further helps to prevent portions of the obstruction from being carried downstream.

The capture element is preferably naturally biased toward the expanded position although the capture element may also be manually actuated as described below. The capture element has a support structure with a flexible cover attached thereto. The support structure preferably has a closed loop which opens the distal end of the cover. The loop is preferably integrally formed and has a number of integrally formed hinges which deflect when the loop is expanded and collapsed. The hinges are preferably V-shaped although other shapes may be used. A plurality of struts extend proximally from the loop.

The capture element may also be expanded by the user so that the user may select the appropriate time for expansion of the capture element. In this manner, the user may advance the capture element to a suitable location for expansion. The user may also collapse the capture element before withdrawing the capture element into a catheter. The capture element has an actuator for opening and closing the capture element. The actuator may have a control arm and a stable arm although any suitable actuator may be used. The control arm is manipulated to expand and contract a loop at the distal end of the capture element. Alternatively, the actuator may be a tube which cinches the loop closed. In a specific embodiment, the capture element may also evert when moving to the expanded position.

The device of the present invention may be used in various different locations and for various different purposes. In one embodiment, the device may be used in connection with a guide catheter. When used with the guide catheter, the device may be expanded to slow or even stop blood flow when performing other procedures downstream of the guide catheter such as removing a clot or placing a stent.

Alternatively, the device may be passed through a conventional guide catheter so that the device may be introduced further into the vasculature. In this system, the capture element passes through the guide catheter. The obstruction engaging device is then used to engage the obstruction and move the obstruction into the capture element.

The present invention is also directed to methods and devices for removing an obstruction where the obstruction engaging element has a shape which traps the obstruction. In one aspect, the element extends proximally and then distally to ensnare the obstruction. The element may have such a shape naturally or may be moved into this shape by manipulating the element. For example, the element may be rotated in one or both directions to ensnare the obstruction. The element may have a portion which prolapses to capture the element as the element is manipulated.

In still another aspect of the invention, the capture element inverts when the obstruction is moved into the capture element. The obstruction is preferably engaged with an engaging element having a filament which ensnares the obstruction. The obstruction engaging element may be independent from the capture element or may be connected to the engaging element. The capture element inverts upon application of a compressive force to the inverting portion or upon any other suitable actuation force. The capture element preferably inverts when the compressive force is applied by either the obstruction or the engaging element.

The present invention is also directed to actuators for medical devices. In a first aspect, an actuator is provided which has an outer member and a plurality of fingers extending from the outer member. The fingers form an end that can be opened and closed by bending and straightening the fingers. The fingers may be bent by moving an inner member coupled to the fingers or by tensioning or releasing tension on a filament. The medical devices described above may be used for any suitable purpose including capture or containment of obstructions. For this purpose, the fingers or frame may be covered with the cover that forms an enclosure to hold the obstruction.

In another aspect, the medical device may have a frame that extends from inner and outer members. The frame forms an end that also opens and closes. The frame has a first set of connectors coupled to the outer member and a second set of connectors coupled to the inner member. The inner and outer members are movable relative to one another to open and close the end. The frame may be an integral structure with the structure being deformed when the end opens and closes. In still another aspect, the frame may be made of a shape memory material which regains either the closed or open position when heated or cooled. For example, the frame may be heated using electrical energy or other suitable source to actuate the frame.

In still another aspect of the present invention, a device and method for removing an obstruction from a blood vessel is provided. A strand extends along the elongate obstruction removing element and extends between the coils of the element. The element may be manipulated to entangle the main element with the strand and to entangle the device with the obstruction. The strand will become entangled with the element at locations dependent upon permitted expansion of the element within the blood vessel.

In yet another aspect, an intravascular device and method for removing material from a vascular site are provided. A filament is wrapped around the main element in a delivery condition. The filament and main element are then rotated relative to one another to cause the two to essentially unravel.

In yet another aspect of the present invention, an obstruction removing element is provided which has a plurality of expandable structures formed by the elongate element. The expandable structures are formed so that adjacent structures wind in opposite directions when viewed along the longitudinal axis of the device. The expandable structures may wind to form a substantially closed structure. To this end, the expandable structure may wind about 360 degrees when viewed along the longitudinal axis. Of course, the expandable structure may wind a bit more or less than 360 degrees such as 315-405 degrees.

These and other advantages of the invention will become apparent from the following description, drawings and claims.

BRIEF DESCRIPTION OF THE DRAWING FIGURES

FIG. 9 shows another obstruction engaging element.

FIG. 10 shows the obstruction engaging element of FIG. 9 with the element engaging an obstruction.

FIG. 11 shows the obstruction engaging element of FIGS. 9 and 10 with the element having a prolapsed portion.

FIG. 12 shows another obstruction engaging element in an expanded position.

FIG. 13 shows another device for removing an obstruction.

FIG. 14 shows the obstruction removing device of FIG. 13 expanded to engage the obstruction.

FIG. 15 shows another obstruction removing device in an expanded position.

FIG. 16 shows still another obstruction removing device.

FIG. 23 shows another obstruction removing device.

FIG. 24 is a side view of the device of FIG. 23.

FIG. 28 shows another obstruction removing device.

FIG. 29 shows another obstruction removing device.

FIG. 30 shows another obstruction removing device.

FIG. 31 is an end view of the obstruction removing device.

FIG. 33 shows another device for removing an obstruction.

FIG. 34 shows the device of FIG. 33 expanded within a blood vessel.

FIG. 38 shows a device having more strands and loops along the proximal section than along the distal section.

FIG. 39 shows the device having an interlocking strand extending between two strand loops.

FIG. 44 shows expansion of part of the main element distal to the obstruction.

FIG. 45 shows expansion of part of the main element within the obstruction.

DETAILED DESCRIPTION OF PREFERRED EMBODIMENTS

Figure 1:
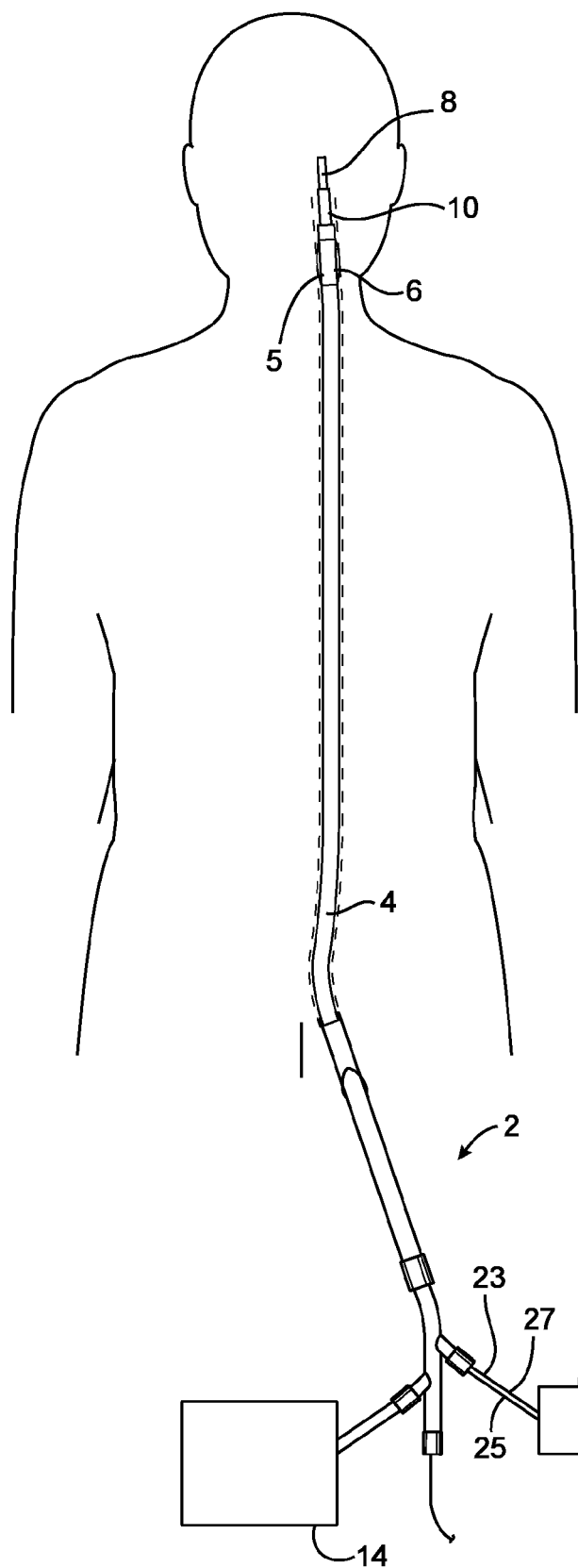
FIG. 1 shows a system for removing an obstruction.
Figure 2:
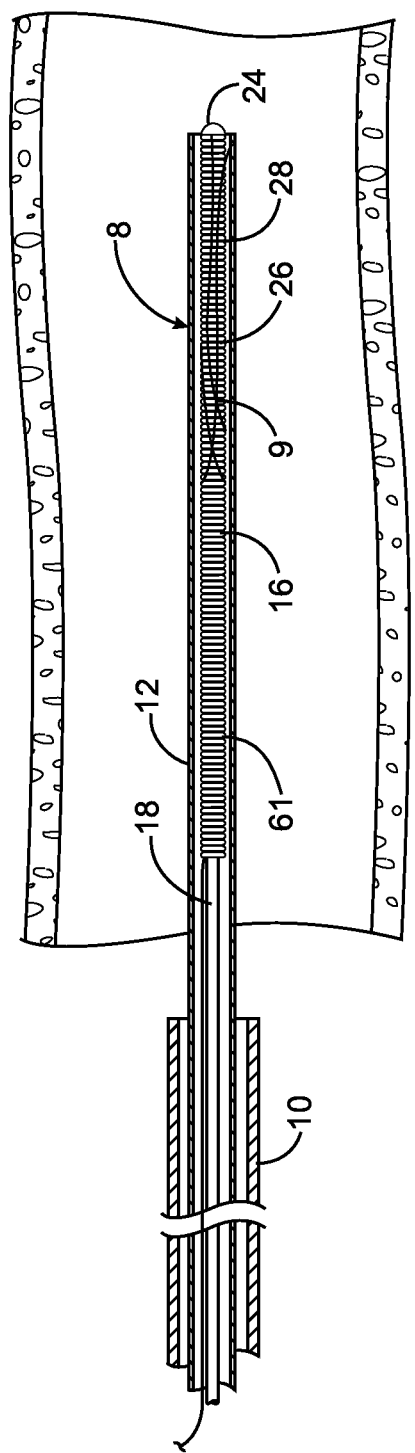
FIG. 2 shows the obstruction removal device in a collapsed condition.

Referring now to FIGS. 1-4, a system 2 for removing an obstruction is shown. A guide catheter 4 is advanced to a location proximal to an obstruction. When accessing the cerebral vasculature, for example, the guide catheter 4 is often positioned in the carotid or vertebral artery. Of course, the guide catheter 4 may not be necessary or may be positioned in any other suitable location depending upon the location of the obstruction. The guide catheter 4 preferably has a flow restricting element 6 which restricts or even stops blood flow through the vessel as described below. The flow restricting element 6 is preferably a balloon 5 coupled to a source of inflation fluid 7 which is used to inflate the balloon 5.

An obstruction removing device 8 is advanced through the guide catheter 4 to the obstruction. A microcatheter 10 may also be positioned within the guide catheter 4 to deliver the obstruction removing device 8 further into the vasculature. The obstruction removing device may be advanced by itself through the microcatheter 10 or may be contained within a sheath 12 which is advanced through the microcatheter 10. A source power 14 may also be coupled to the obstruction removal device 8 for use in the manner explained below. The power source 14 may simply produce a positive or negative charge or may be an RF or other suitable power source.

Figure 3:
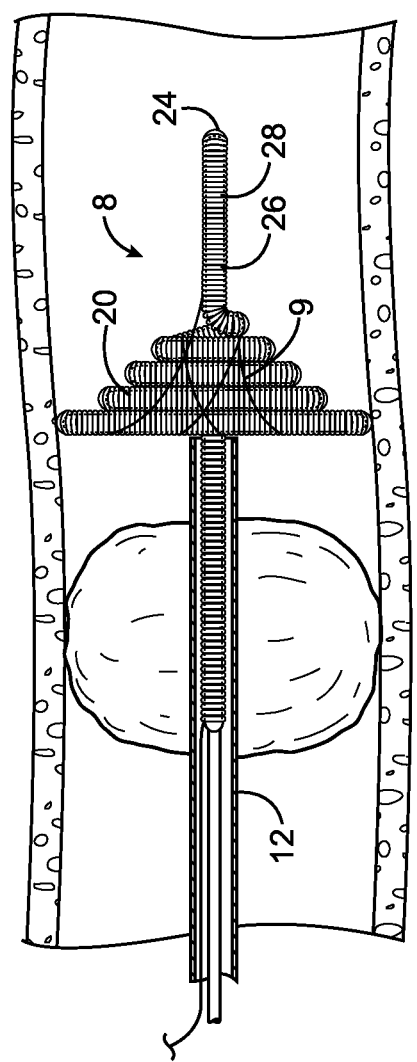
FIG. 3 shows the obstruction removal device with a distal portion of the obstruction removal device expanded.
Figure 4:
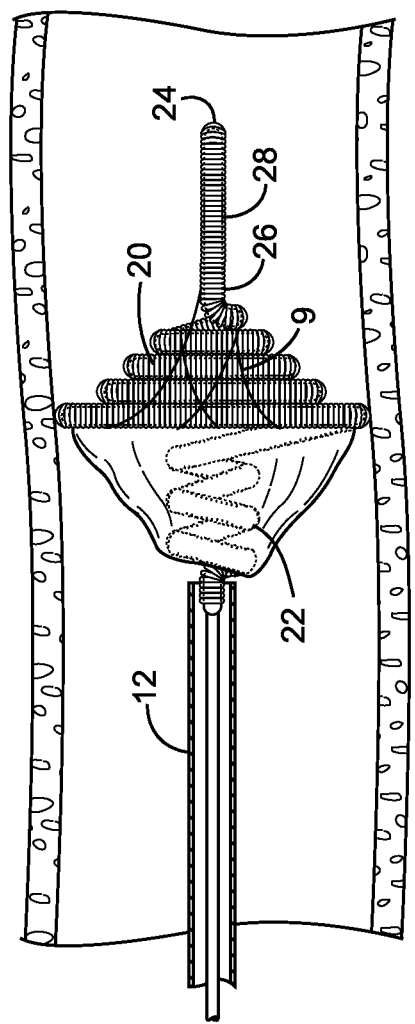
FIG. 4 shows the obstruction removal device with a proximal portion expanded to engage an obstruction.
Figure 5:
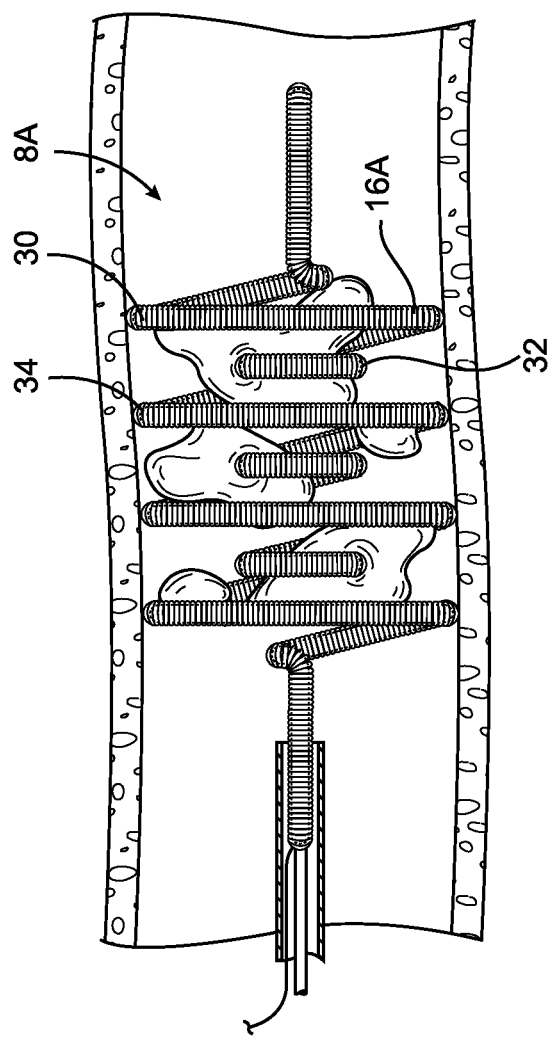
FIG. 5 shows another obstruction removal device.
Figure 6:
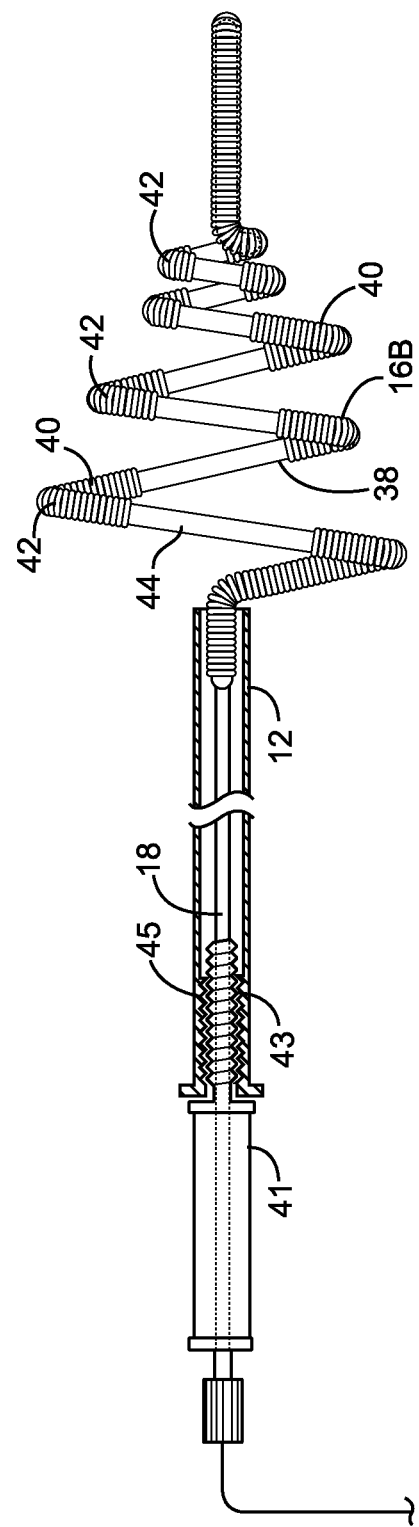
FIG. 6 shows yet another obstruction removal device.
Figure 7:
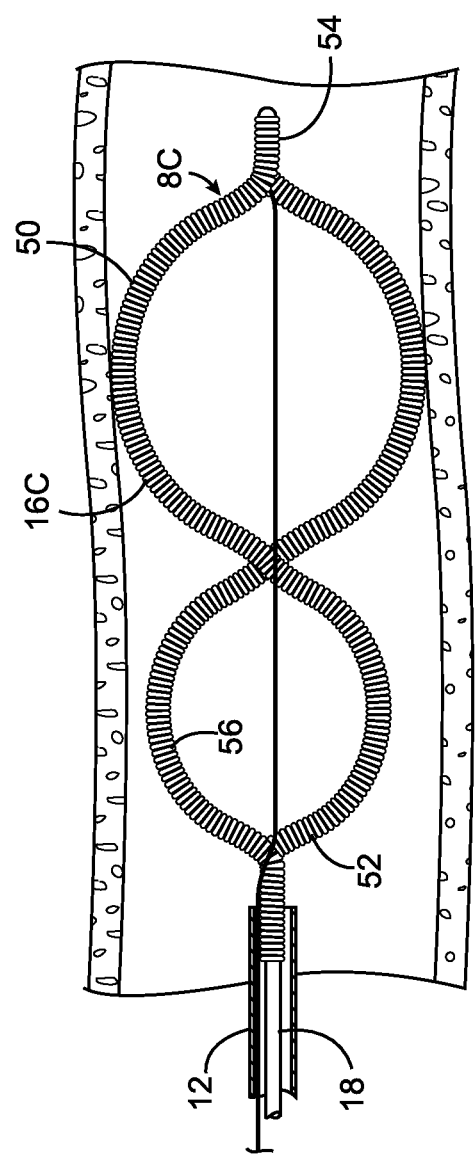
FIG. 7 shows still another obstruction removal device.

The obstruction removing device 8 has an engaging element 16 extending from an insertion element 18. The engaging element 16 is movable from a collapsed position (FIG. 2) to an expanded position (FIGS. 3 and 4). When the engaging element 16 is contained within the sheath 12 or microcatheter 10, the engaging element 16 is in a relatively straight configuration. The engaging element 16 has a distal portion 20, which forms a relatively closed structure, which can catch or trap the obstruction, or any part thereof, to prevent migration of the obstruction or part thereof. The engaging element 16 has a proximal portion 22 which is formed with smaller coils than the distal portion 20. The proximal portion 22 engages the obstruction as described below.

Figure 8:
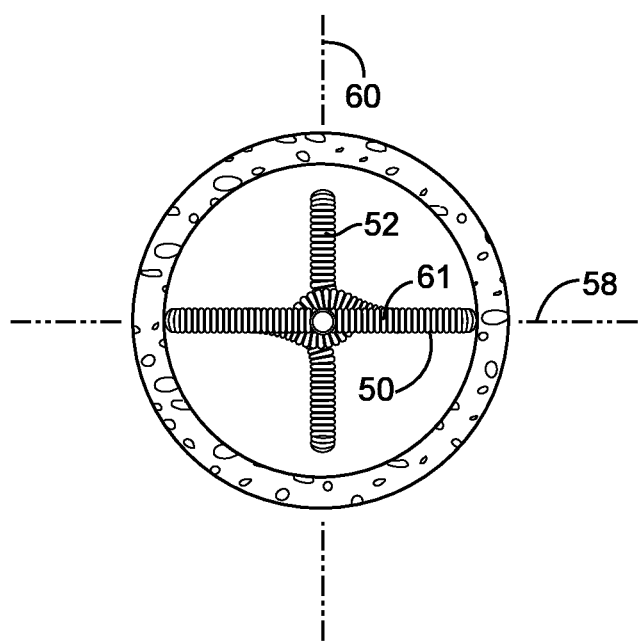
FIG. 8 is an end view of the obstruction removal device of FIG. 7.

An advantage of the obstruction removal device 8C is that the loops 50, 52 exert substantially equal and opposing forces on the sheath 12 or microcatheter 10 through which the obstruction removal device 8C is advanced. In this manner, kinking or binding of the obstruction removal device 8C during advancement can be minimized or reduced altogether. Referring to the end view of FIG. 8, the first and second loops 50, 52 preferably lie in first and second planes 58, 60, respectively, which are preferably perpendicular to one another.

Another method of aiding mechanical capture of an obstruction is to coat the device and elements of the present invention with a material 61 which helps to adhere the obstruction, and in particular thrombus, to the device or element. The material 61 is preferably fibrin but may be any other suitable material. Use of the material 61 may be incorporated into any of the devices described herein or other suitable device such as the devices shown in FIG. 2-8, 22 or 30.

Referring to FIGS. 9-12, another obstruction engaging element 270 is shown. The obstruction engaging element 270 includes a filament 272 which forms windings or coils 274. The windings 274 may take any suitable shape such as helical. The obstruction engaging element 270 is advanced to an obstruction in any manner described herein. For example, the obstruction engaging element 270 may be contained within the sheath 12 or catheter 10 (FIGS. 1 and 2) and advanced through the obstruction. The obstruction engaging element 270 is then advanced out of the sheath 12 or catheter 10 (FIGS. 1 and 2) to permit the obstruction engaging element 270 to expand.

When the element initially expands, the coils 274 do not overlap when viewed along a longitudinal axis L. The element 270 is then engaged by manipulating the element 270. After the obstruction has been engaged, the element 270 is rotated which tends to open the coils 274. This causes one or more proximal coils 274 to prolapse over other coils to ensnare the obstruction. Stated another way, the element 270 initially extends distally in a relatively continuous manner. After rotating the element 270, the element extends distally, then proximally, then distally again. Stated yet another way, the coils are manipulated so that they appear to overlap when viewed along the longitudinal axis L. The prolapsed or overlapping coils 274 may provide an even more secure engagement to the obstruction. The element 274 may also be formed to have the overlapping or prolapsed sections when in the natural, unbiased and expanded position as shown in FIG. 11.

Referring now to FIGS. 13 and 14, still another device 280 for removing an obstruction is shown. The device 280 may be used in any suitable manner described herein. For example, the device 280 may be advanced by itself or advanced while contained in a sheath or catheter. The sheath or catheter 281 holds the device 280 in a substantially straight configuration. The device 280 has an elongate element 282, such as a wire 284, which expands to the expanded shape of FIG. 14 similar to other embodiments described herein. The elongate element 282 has a distal end 286 coupled to an insertion element 288. A proximal end 290 of the elongate element 282 is coupled to a collar 292, which slides on the insertion element 288. Sliding of the collar 292 permits the elongate element 282 to move between the collapsed and expanded positions of FIGS. 13 and 14. The insertion element 288 also has a stop 294, which prevents movement of the collar 292 beyond the position of FIG. 14. The device 280 may also have a pull wire 289. The pull wire 289 may not be needed to hold the element 282 in the collapsed position since the catheter 281 may be used to hold the element in the collapsed position 282. The pull wire 289 gives the user the ability to collapse the element 282 if needed after deployment. The element 282 may, of course, take other shapes such as a double-helix which would include the dotted-line structure as well.

Still another device 300 is shown in FIG. 15. The device 300 is similar to many of the other devices described herein and may be used in any manner described herein. The device 300 is formed by an elongate element 302, such as a wire 304, which forms a number of coils 306. The device 300 has larger coils 308 at a distal portion 310 and smaller coils 312 along an intermediate portion 314. The smaller coils 312 are preferably stiffer than the larger, distal coils 308. In this manner, excessive elongate of the device can be reduced since the stiffer coils 312 help to resist elongation of the element 302 when the element is pulled. The device 300 is also particularly useful when using the following routine to remove an obstruction. The device 300 is positioned in a catheter or sheath which is advanced through the obstruction. The distal coils 308 are expanded distal to the occlusion but may be expanded within the obstruction as well. The device 300, and catheter if necessary, are then manipulated to expose the intermediate portion 314 within the obstruction. The intermediate portion 314 expands within the obstruction and engages the obstruction. The stiffer, intermediate portion 314 resists elongation when withdrawing or moving the obstruction so that the device 300 maintains good contact with the obstruction. The larger, distal coils 308 help to trap the obstruction and prevent parts of the obstruction from trailing or escaping removal. The device 300 also has a proximal portion 316, which may be expanded proximal to the occlusion so that the occlusion is substantially trapped between the proximal and distal portions 316, 310.

Referring to FIG. 16, another device 319 is shown which is similar to the device of FIG. 15. The device 300 has distal, intermediate and proximal portions 318, 320, 322. The proximal portion 322 differs from the proximal portion 316 of FIG. 15 in that the proximal portion 322 winds distally, then proximally, then distally again. The back-and-forth winding of the proximal portion 322 increases the stiffness of the proximal portion 322 which may help resist elongation of the device during withdrawal of the obstruction. If the device begins elongating during manipulation of the obstruction, the obstruction will engage the proximal portion which then helps to resist further elongation of the device. The device 319 may be used in the manner described above in connection with FIG. 15 in that the intermediate portion may be deployed within the obstruction.

Figure 17:
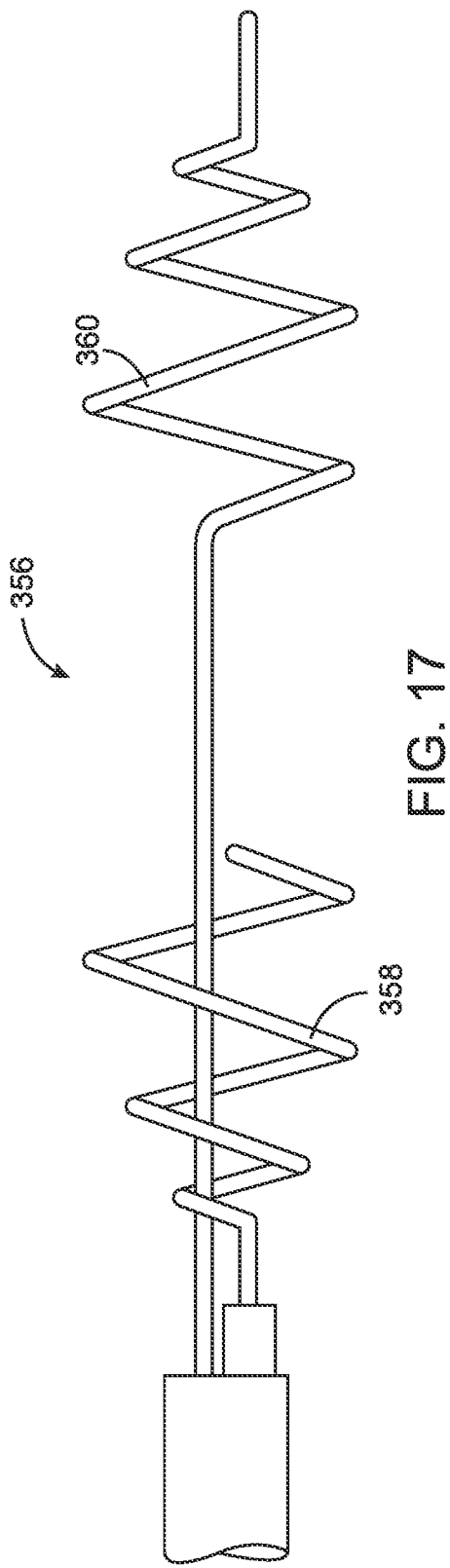
FIG. 17 shows an obstruction removing device having independently movable proximal and distal portions.

Referring to FIG. 17, still another device 356 is shown for removing an obstruction. The device 356 has a proximal obstruction removing element 358 and a distal obstruction removing element 360. The elements 358, 360 are preferably independent so that they may be manipulated independently. Each of the obstruction removing elements 358, 360 may be any of those described herein or any other suitable structure. In one aspect of the invention, the distal obstruction removing element 360 may be deployed within or distal to the obstruction. The other element 358 is deployed on the proximal side of the obstruction, or within a proximal portion of the obstruction, to provide further control and entrapment of the obstruction. The proximal obstruction removing element may also be used to resist and prevent excessive elongation of the distal obstruction removing element 360 when the distal removing element 360 is pulled to move the obstruction. The elements 358 may extend through the same multi-lumen catheter or may be provided in separate catheters without departing from the scope of the invention.

Figure 18:
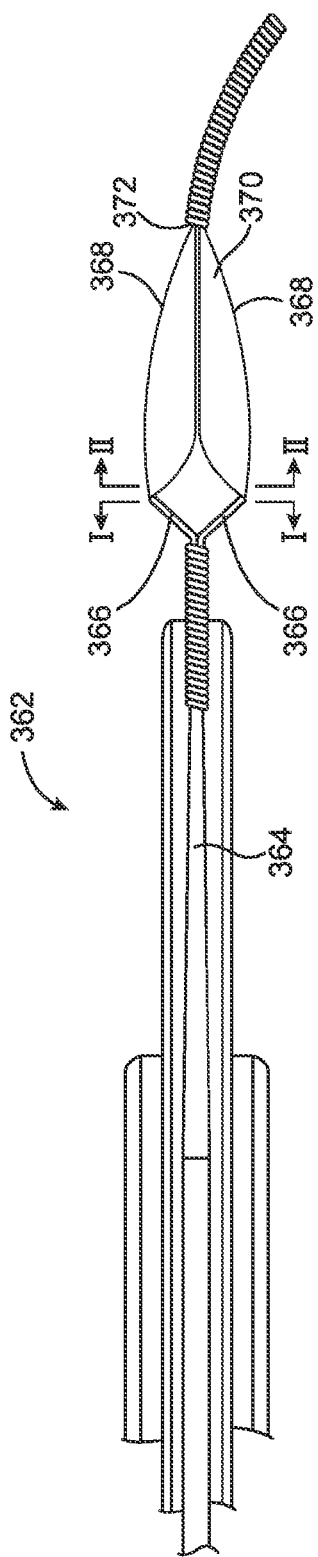
FIG. 18 shows still another obstruction removing device.
Figure 20:
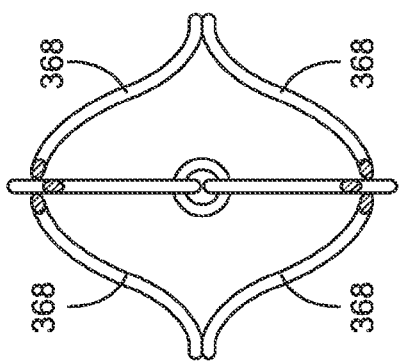
FIG. 20 is a cross-sectional view of FIG. 18 along line II-II.
Figure 19:
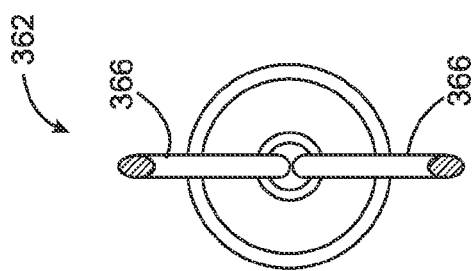
FIG. 19 is a cross-sectional view of FIG. 18 along line I-I.
Figure 64:
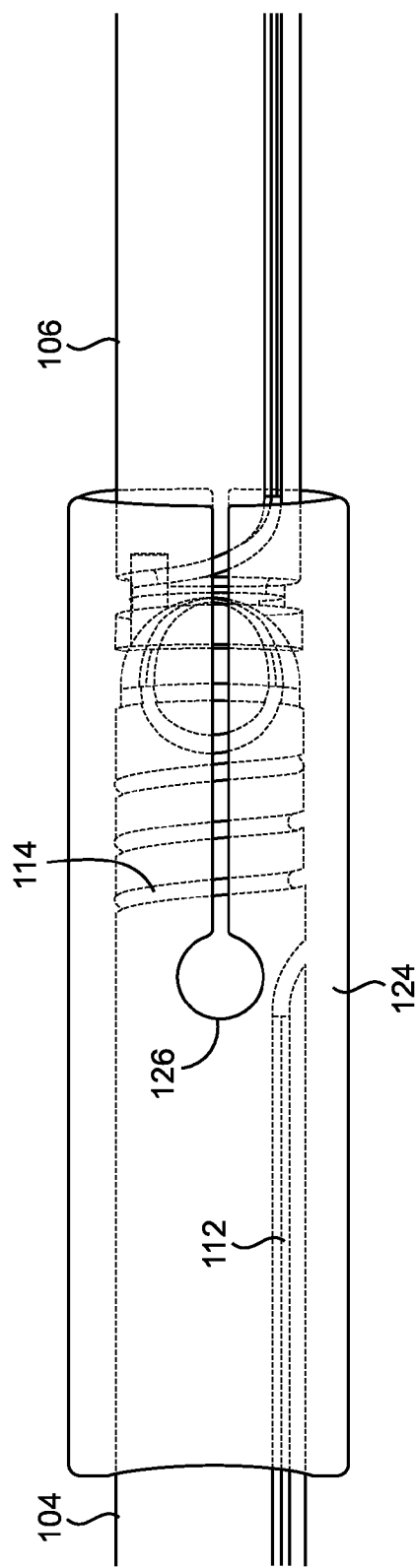
FIG. 64 shows an enlarged view of the keyhole sleeve positioned over the mandrel.

Referring to FIGS. 18-20, still another device 362 for removing an obstruction is shown. The device 362 has an insertion element 364 and struts 366, preferably 2-4, extending from a distal end of the insertion element 364. Arms 368 extend from the struts 366 to form a cage-like structure 370. The device 362 preferably has at least two arms 368, preferably 2-4 arms, extending from the end of each strut 366. For example, FIG. 64 shows two struts 366 with three arms 368 extending from each strut 366. In another example, three struts 366 may be used with two arms 368 extending from each strut 366. The struts 366 are relatively short when viewed along the longitudinal axis and may be less than ½, and more preferably less than ⅓, the length of the arms 368. The distal end of the arms 368 are coupled together to form a tip 372 of the cage-like structure 370.

Figure 22:
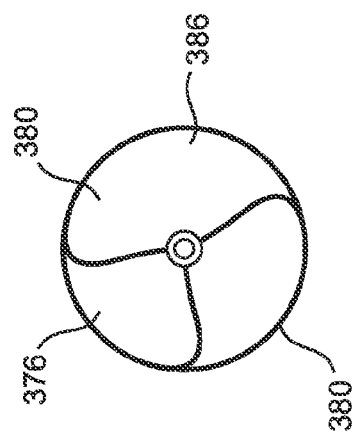
FIG. 22 is an end view of FIG. 21 showing a larger opening between some of the wires.
Figure 21:
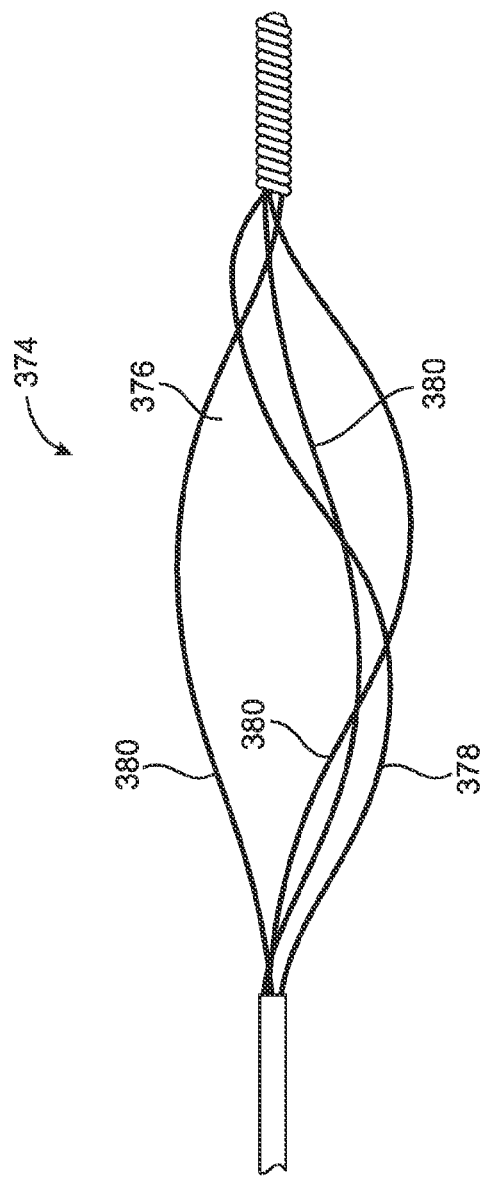
FIG. 21 shows another obstruction removing device.

Referring now to FIGS. 21 and 22, still another device 374 is shown for removing obstructions. The device 374 has a cage-like structure 376 formed by a number of elongate elements 378 such as wires 380. The wires 380 are coupled together at proximal and distal ends 382, 384 to form the cage-like structure. The wires 380 may be substantially independent and are preferably not braided or woven. The elongate elements 378 may be wound helically, although other shapes and patterns may be used, with the elements 378 all wound in the same direction. Although cross-members or cross-elements may be provided, it is preferably to omit such cross-members and cross-elements. An advantage of providing the relatively independent elements 378 is that the entire structure may be collapsed to a smaller size than typical woven or braided elements. Referring to FIG. 22, an end-view of the device 374 shows that a larger spacing 386 between two of the wires 380 to permit the obstruction to pass into the opening. The other end, such as the distal end, preferably has a more symmetrical pattern to minimize the size of the openings and prevent the obstruction from escaping through the distal end. The proximal portion may also form larger coils than the distal section so that the obstruction may pass through openings in the proximal portion but is prevented from escaping through the distal end.

Figure 25:
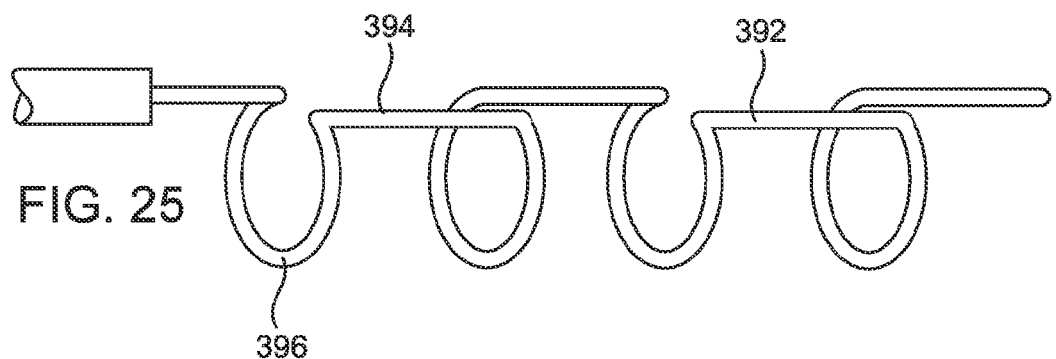
FIG. 25 shows another obstruction removing device.
Figure 26:
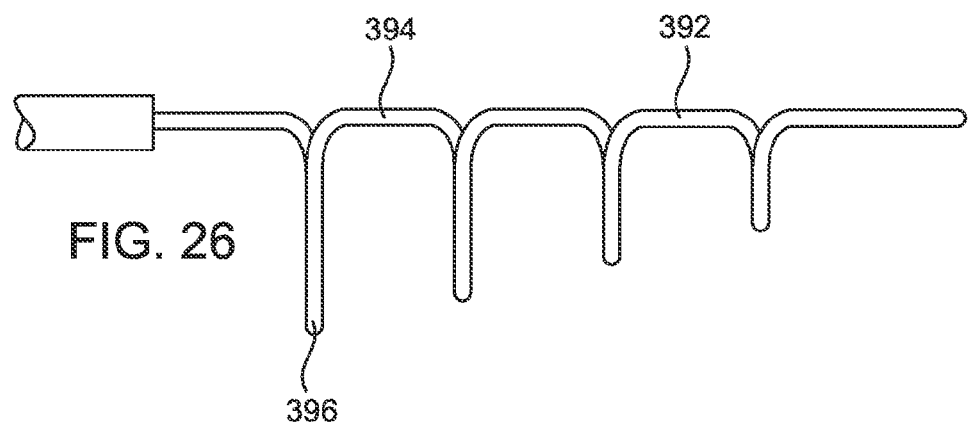
FIG. 26 is a side view of the device of FIG. 25.
Figure 27:
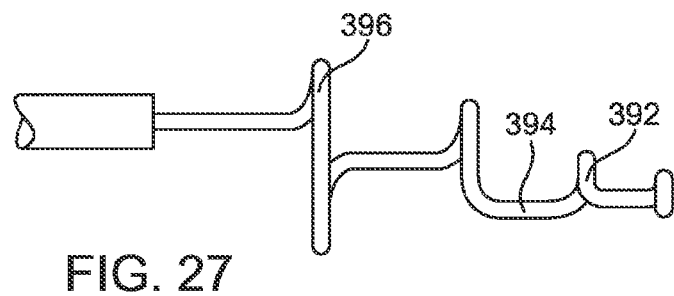
FIG. 27 is an alternative side view of the device of FIG. 25.
Figure 32:
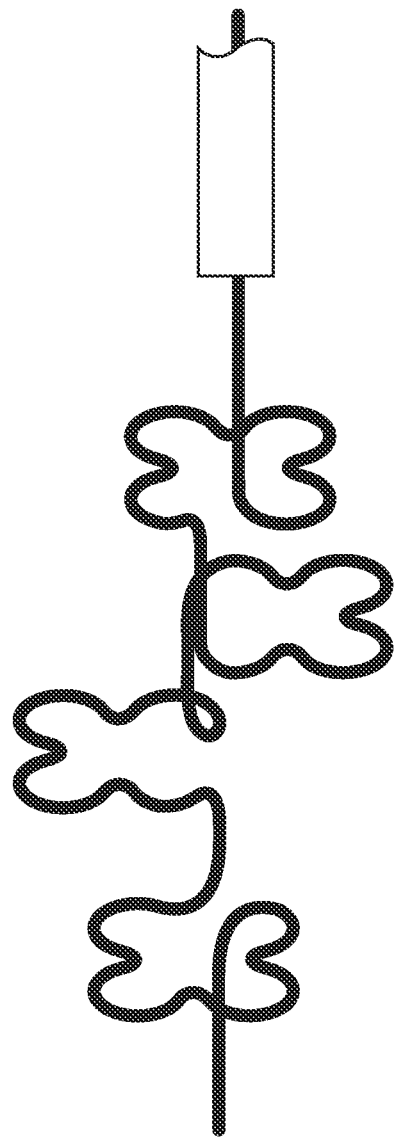
FIG. 32 shows another obstruction removing device.
Figure 35:
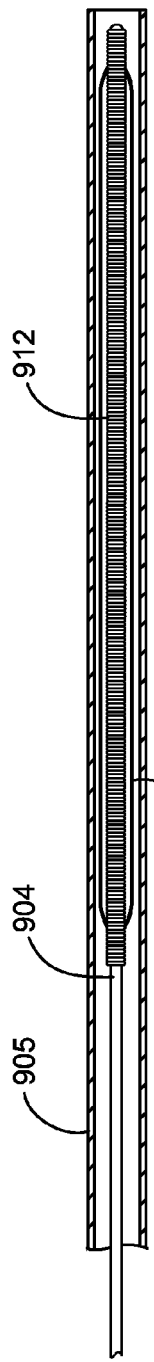
FIG. 35 shows another device for removing an obstruction in a collapsed position.

Referring now to FIGS. 23-32, various other devices for removing an obstruction are shown. The devices are held in a substantially straight, collapsed position when contained in a sheath or catheter as described herein. Referring to FIG. 23, an elongate element 392, such as a wire 394, forms a number of discrete structures 396 when permitted to expand. The discrete structures 396 may take any shape such as a circular structure (FIG. 25), or a flower-petal like structure (FIGS. 23 and 28-31). In one aspect, the structures 396 may be substantially parallel to one another (FIG. 24). In another aspect, the discrete structures extend from a side of an otherwise straight portion of the wire (FIG. 26) or may be centered with respect one another (FIG. 27). The discrete structure 396 may also have different sizes (FIGS. 26 and 27). The discrete structures 396 may also be oriented to create an interfering pattern as shown in the end view of FIG. 31. The discrete structures 396 may also be formed somewhat continuously as shown in FIG. 32.

Referring to FIGS. 33-41, still another device 902 for removing an obstruction is shown. The device 902 has a main element 904 that may be any suitable element 904 such as those described herein. The element 904 is held in a substantially straight, collapsed position within the delivery catheter 905 as described above. Similar to the embodiment of FIGS. 2 and 3, the element 904 has one or more strands 906 which extend along the element 904. Of course, the strands 906 may extend freely alongside the main element 904 or may be wound helically, interwoven or interlocked with the element 904 without departing from the scope of the invention. The strands 906 are tied, knotted, looped, soldered, or otherwise attached to the main element 904 at the ends of the expandable portion of the main element 904. Of course, the strands 906 may be looped around or attached to the main element 904 at other parts of the main element 904. For example, the strand 906 may be attached or coupled to the main element 904 several centimeters proximal to the expandable portion of the main element 904 without departing from the scope of the invention.

Figure 36:
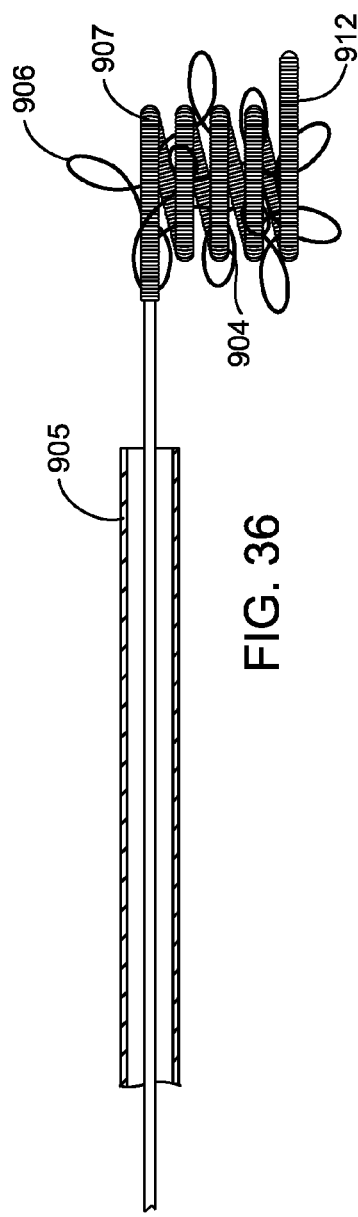
FIG. 36 shows one possible configuration for the expanded device of FIG. 35.
Figure 37:
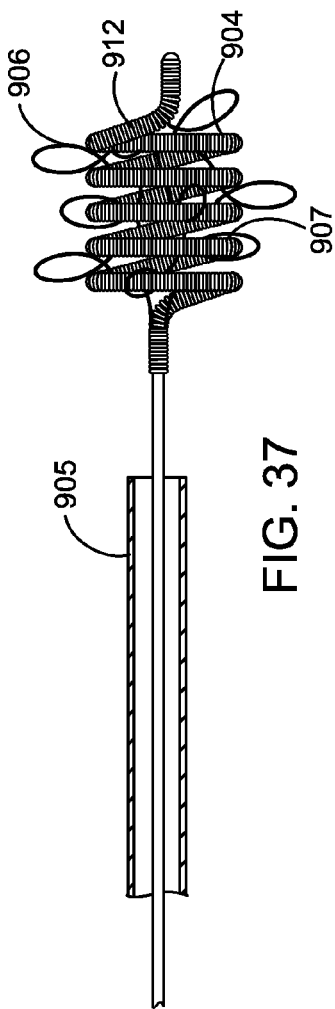
FIG. 37 shows another possible configuration for the expanded device of FIG. 35.
Figure 40:
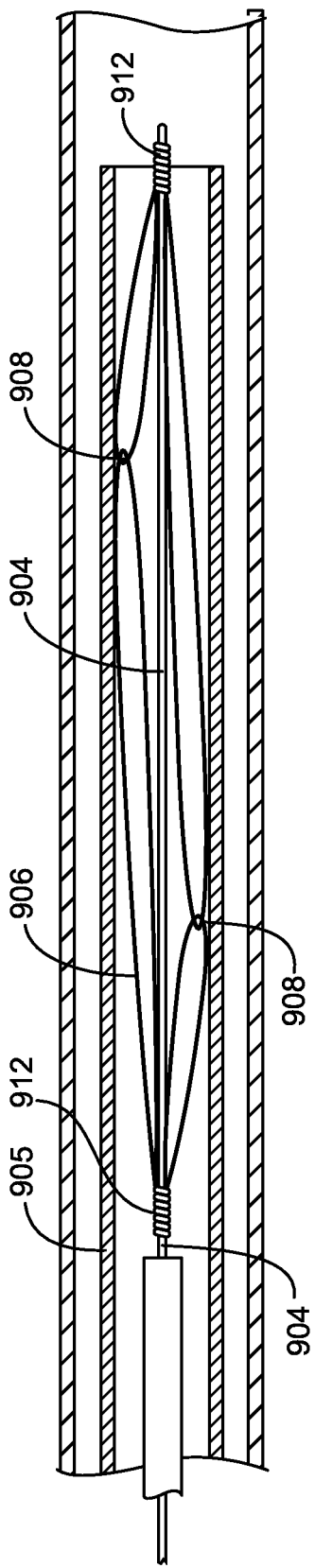
FIG. 40 shows the strand loops interlocking closer to the distal and proximal ends in the upper and lower parts, respectively.

The main element 904 may be any suitable element 904 which is naturally biased toward the expanded position such as any of the elements described herein. FIGS. 34, 36 and 37 show three different embodiments of the main element 904 for purposes of illustration. The main element 904 may form helical coils 907 having varying diameter as shown in FIG. 34 or may have coils 907 with the same diameter as shown in FIG. 37 or may even have coils 907 which extend transverse to the longitudinal axis as shown in FIG. 36. Of course, any suitable shape may be used for the main element 904.

The strand 906 may be any suitable filament, wire, fiber, monofilament and may be made of any suitable material such as nylon, polypropylene, polyester, polyurethane, silicone, latex, a liquid crystal polymer (LCP) such as Vectran or even nitinol or stainless steel. The strand 906 is flexible and may not have a predetermined shape with the strand 906 being deformed and deflected by the element 904 as the element 904 expands. The element 904 includes two strands 906 which interlock or have interlocking loops 908 at about the midpoint of the expandable portion of the element 904. Stated another way, the strands 906 form two loops 908 which interlock at the midpoint as shown in FIG. 33. The strands 906 and loops 908 are shown in an exaggerated state in the collapsed position of FIG. 33 for clarity. Of course, one advantage of the invention is that the strands 906 are relatively small and flexible and do not take up much space in the lumen of the delivery catheter as compared to conventional structures using wires and the like. This feature cannot be appreciated, of course, in the exaggerated depiction of FIG. 33.

Figure 41:
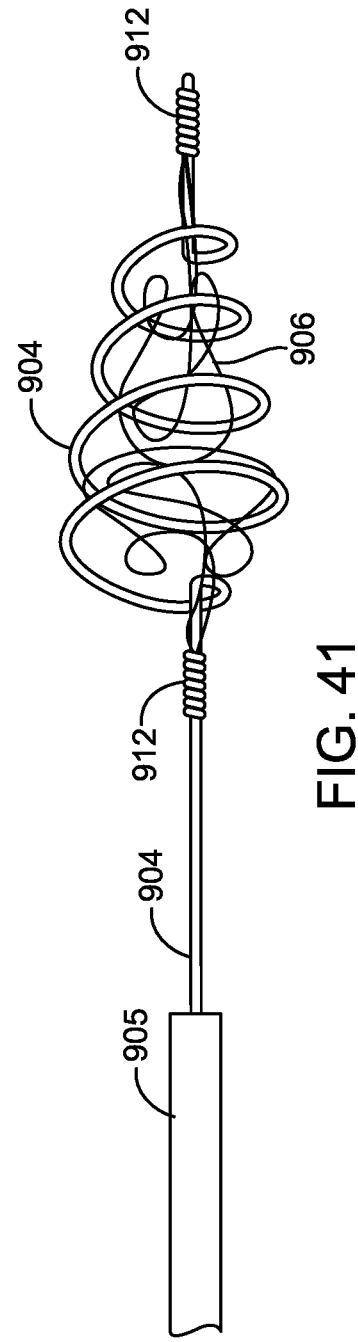
FIG. 41 shows the strands positioned within the expanded shape of the main element.
Figure 42:
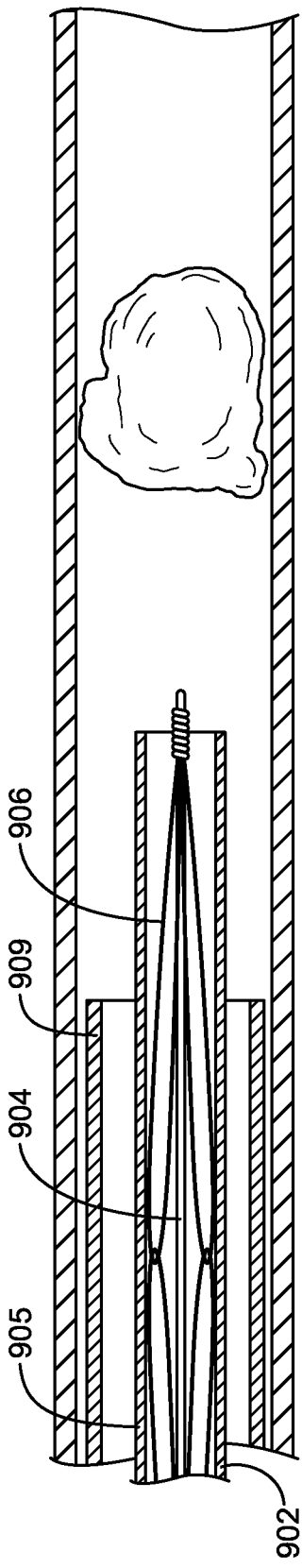
FIG. 42 shows the device positioned proximate to an obstruction.

Referring to FIG. 38, the strands 906 may also form more loops 908 on one side than on the other. An interlocking loop 910 extending around the main element 904 may also be provided to interlock pairs of loops 908 as shown in FIG. 39. The strands 906 or loops 908 may also intersect nearer to the proximal or distal ends as shown in the upper and lower parts of FIG. 40. Referring to FIG. 41, the strands 906 may also be positioned generally inside the element 904 when the element 904 is expanded. The device may be loaded by pulling the ends of the element 904 when in the position of FIG. 37 to collapse the main element 904 around the strands 906. The device is then restrained in the delivery catheter 905 and delivered to the obstruction.

Referring again to FIGS. 34-37, the main element 904 may have a filament 912, such as platinum coil, wound around the expandable portion of the main element 904. The filament may help to improve radiopacity and may also be sized and configured so that the strand 906 can be held between adjacent windings of the filament 912 to enhance interlocking engagement between the strand 906 and element 904. Alternatively, the filament 912 may only be provided at the ends of the expandable portion of the main element 904 as shown in FIG. 34 where the strands 906 are coupled to the main element 904.

Figure 43:
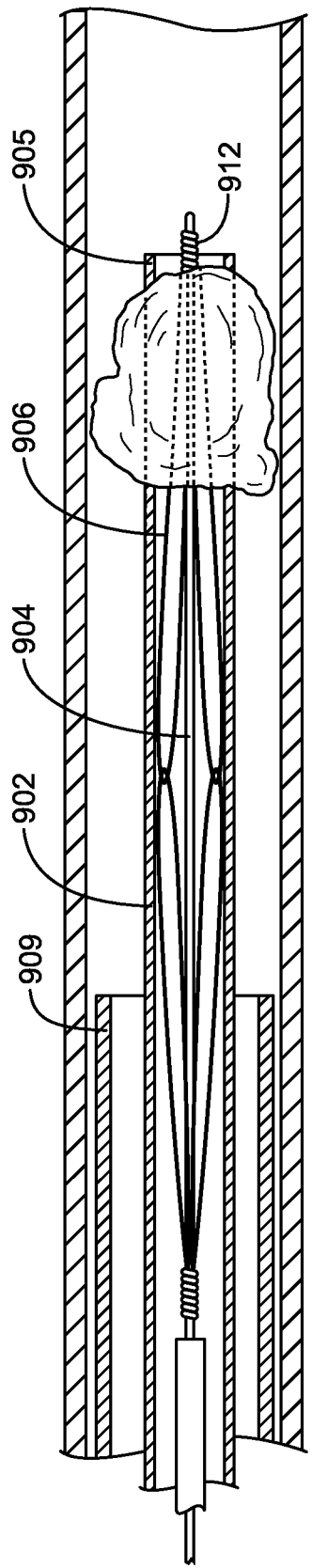
FIG. 43 shows the device advanced into and through the obstruction.
Figure 46:
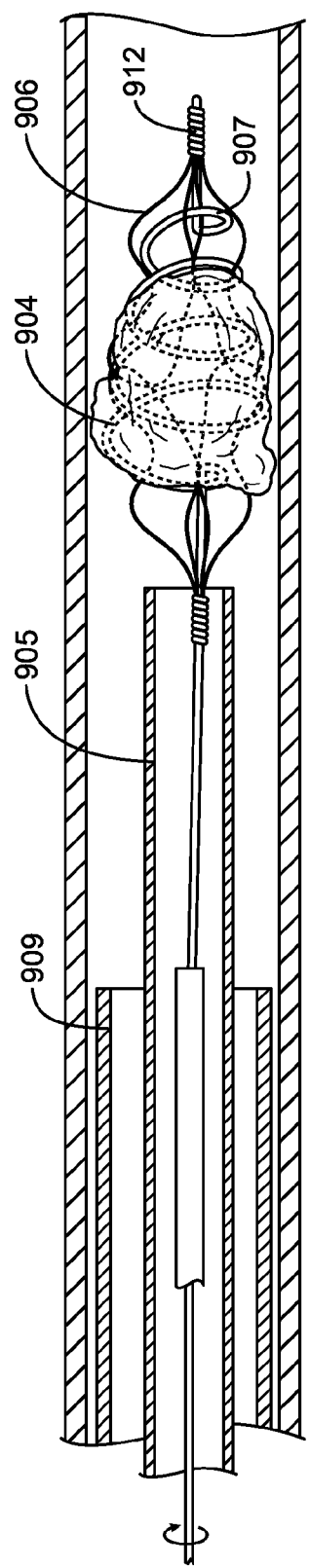
FIG. 46 illustrates that rotation of the main element causes the strand to become entangled with the main element and enhances engagement between the device and the obstruction.

Use of the devices 902 of FIGS. 33-41 is now described with further reference to FIGS. 42-46. The delivery catheter 905 is passed through the obstruction so that the distal tip is beyond the obstruction as shown in FIG. 43. The main element 904 is then expanded so that one or more coils are distal to the obstruction as shown in FIG. 44. The delivery catheter 905 is then withdrawn further to expose more of the expandable portion of the main element 904 as shown in FIG. 45. Although it is preferred to position one or more coils distal to the obstruction, all or part of the expandable portion of the main element 904 may be expanded within, distal or even proximal to the obstruction without departing from the scope of the invention.

The device 900 may emerge from the delivery catheter 905 with the strands 906 being relatively free of the main element 904 between the proximal and distal attachments to the main element. Of course, the strands 906 may be interwoven, looped around or even somewhat entangled with the main element 904 so long as the user may manipulate the device to further entangle the strand 906 and element 904. Rotation of the device causes the strands 906 to become entangled with the main element 904 in a manner dictated by the geometric restrictions of the vessel and obstruction. The device itself may also become more entangled with the obstruction during rotation of the main element 904. An advantage of using the helical or coiled structures described herein is that rotation of the main element 904 not only causes the device to engage the obstruction but also causes the strand 906 to become entangled with the main element 904.

Another aspect of the present invention is that the amount of entanglement between the strand 906 and element 904 may be controlled. For example, the user may first attempt to remove the obstruction with little or no rotational manipulation of the element 904. The user can then pull on the main element 904 and determine whether the device can remove or dislodge the obstruction or whether the main element is disengaging or slipping relative to the obstruction. Disengagement can occur due to excessive elongation or distortion of the main element 904 or may be simply due to poor engagement between the device and obstruction. The user may then rotate or otherwise manipulate the device to cause further entanglement between the strand 906 and element 904 and between the device itself and the obstruction. Increasing the entanglement between the strand 906 and main element 904 may help to reinforce the main element which can reduce stretching and distortion of the main element 904 when the main element 904 is tensioned. The strands 906 also increase the overall surface area of the device and generally reduce the size of interstitial spaces in the main element 904. Another aspect of the present invention is that the strand 906 and element 904 may engage one another at locations dependent upon the permitted expansion of the main element 904 within the vessel. As such, the present invention provides advantages over conventional mesh-like structures having a predetermined geometry since these structures may not perform adequately under a variety of different size restrictions in an obstruction.

Although the strand 906 and element 904 may not be substantially entangled when the element is initially expanded, the main element 904 and strand 906 may also be designed to become entangled with one another during expansion of the main element 904. For example, the element 904 may naturally begin to twist in a helical manner to form coils 908 when expanding. The twisting motion causes the strand 906 to engage, contact and and/or otherwise entangle itself with the element 904 and obstruction. The strand 906 will engage the element 904 at a number of locations dependent upon the manner in which the element expands within the vessel as described above. Although the element 904 generally follows a helical path when expanding, the element 904 may expand in any other manner which tends to entangle the strand 906 and element 904. For example, the element 904 may rotate one way and then another or may be longitudinally displaced or reciprocated. Thus, it can be appreciated that the element may expand in a number of different ways to cause the strand 906 to become entangled with the element. Of course, the element may also be rotated or otherwise manipulated to enhance entanglement between the strand 906 and element even after expansion of the main element to provide the advantages described above.

After the obstruction has been engaged by the device, the main element is pulled to dislodge the obstruction for removal as describe above. Once the element has dislodged the obstruction, the obstruction may be moved into a guide catheter 909 or sheath for removal from the patient. The guide catheter 909 may have a balloon to occlude blood flow during withdrawal of the obstruction.

Figure 47:
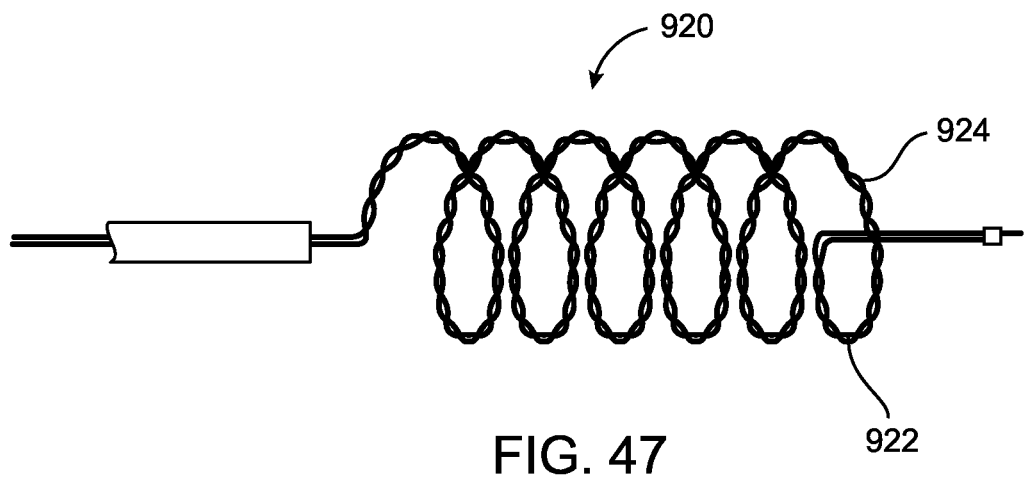
FIG. 47 shows still another device for removing an obstruction.
Figure 48:
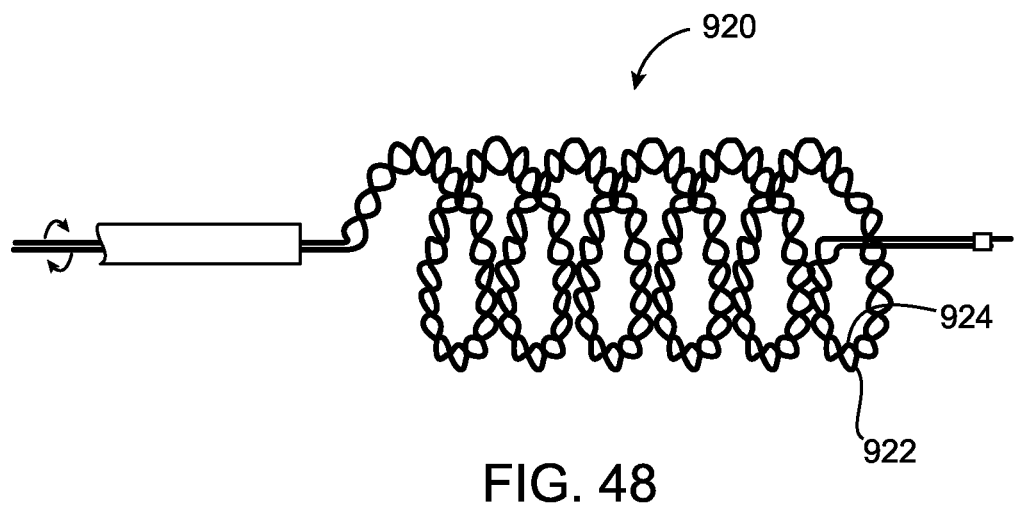
FIG. 48 shows the device of FIG. 47 with the device expanded.

Referring to FIGS. 47 and 48, still another device 920 is shown having at least two filaments 922, 924 with one being wound around the other. The device 920 may be used for any procedure such as those described herein or other suitable procedures. The device 920 can be collapsed and expanded similar to the other devices described herein. The device 920 may take any of the shapes described herein such as generally helical with a number of coils 922. The filaments 922, 924 may be the same or one of the filaments may be a main filament 922 with a more flexible filament 924 wound around the main filament 922.

The filaments 922, 924 may be twisted relative to one another so that they can unwind by manipulating one or both filaments as shown in FIG. 48. When the filaments 922, 924 are unwound, the device has an increased surface area and a reduction in void size. In one mode of operation, the filaments 922, 924 are deployed as shown in FIG. 48 after the device has been expanded to the position of FIG. 47. The filaments 922, 924 may then be twisted to create gaps between the filaments 922, 924. The device may then be used in the same manner as other devices described herein to remove an obstruction or for some other purpose within the patient.

Figure 49:
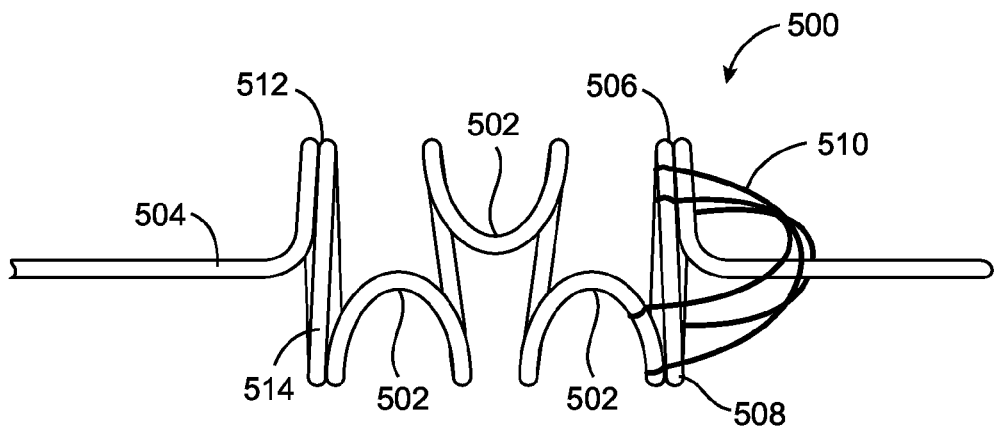
FIG. 49 shows a distal end of another device for removing obstructions from a patient.

Referring to FIG. 49, another obstruction removing device 500 is shown which is similar to the device of FIG. 25. The obstruction removing device 500 also has a number of expandable structures 502 formed by an elongate element 504. The elongate element 504 may extend to a free end similar to other embodiments described herein. The obstruction removing device 500 is similar to the obstruction removing device shown in FIG. 25 in that the device 500 has a number of expandable structures 502 formed one after the other by the elongate element 504. Similar to the embodiment of FIG. 25 the adjacent structures 502 are wound in opposite directions when viewed along the longitudinal axis of the device 500. Each of the expandable structures 502 winds from 315 to 405 degrees in one direction with the device 500 having at least three expandable structures 502. The structures 502 may be loop shaped structures similar to the circular and petal-shaped structures of FIGS. 23-32. The structures of FIG. 49 are formed in a continuous manner as compared to the structures of FIG. 32 which are separated by substantially longitudinally extending sections of the elongate element.

The device 500 may also include a distal section 506 having one or more loops 508 wound in the same direction. The loops 508 may be formed so that residual stresses in the material bias the loops 508 toward one another. In this manner, the loops 508 preserve a tight pitch to engage and even clamp the obstruction as described below. The manner in which the loops 508 of the distal section 506 interact may also influence the configuration of one or more filaments 510 attached to the device 500.

The device 500 may also have a proximal section 512 positioned proximal to the expandable structures 502. The proximal section 512 may also have one or more loops 514 wound in the same direction with a relatively tight pitch. The proximal section 512 may help to surround the obstruction and may also pinch or trap the obstruction between adjacent loops 514 of the proximal section 512 or between the proximal section 512 and one or more of the expandable structures 502.

Figure 50:
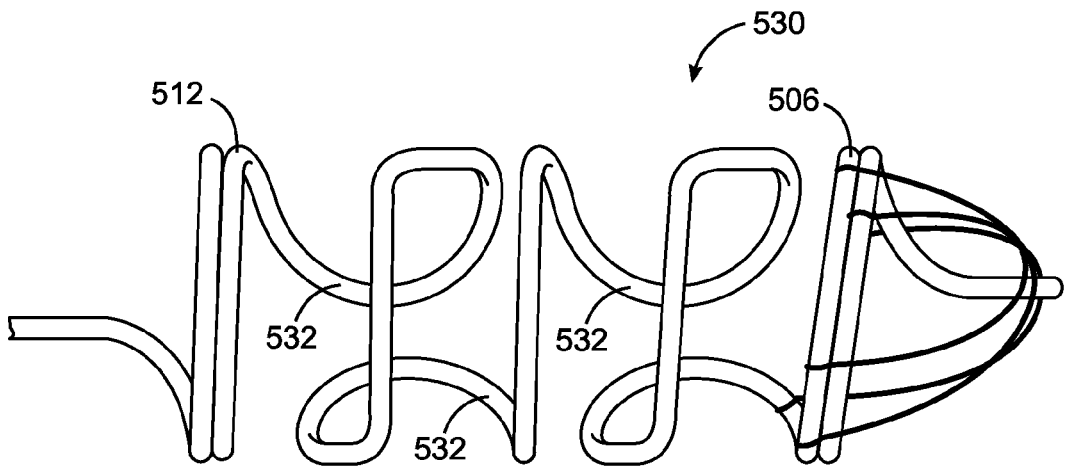
FIG. 50 shows a distal end of yet another device for removing obstructions from a patient.
Figure 51:
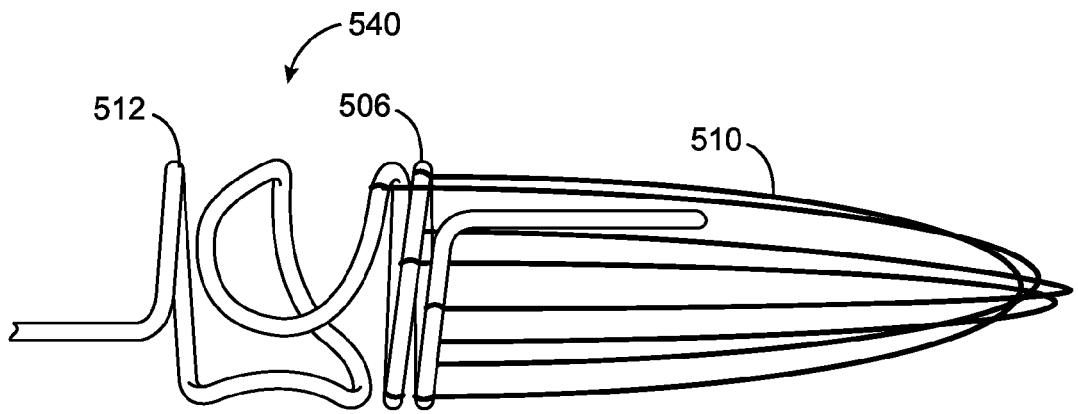
FIG. 51 shows a distal end of still another device for removing obstructions from a patient.

Referring now to FIG. 50, yet another device 530 for removing an obstruction from a blood vessel is shown. The device 530 is similar to the devices of FIGS. 32 and 49 in that the device 530 also forms a plurality of expandable structures 532 which wind in one direction and then the other. The structures 532 may wind as described above in each direction with the device 530 having at least three expandable structures 532. Referring now to FIG. 51, still another device 540 for removing an obstruction from a blood vessel is shown. The device 540 is similar to the devices of FIGS. 32, 50 and 51 in that the device 540 also forms a plurality of expandable structures 542 which wind in one direction and then the other. The expandable structures 532, 542 of devices 530, 540 have relatively complex shapes which not only wind in one direction and then the other but also extend proximally and distally when forming the structures.

The devices 500, 530, 540 may also include one or more of the filaments 510 coupled to the elongate element 504. The filaments 510 may be positioned and configured in any manner described herein and the features and advantages of the filament 510 described herein and in the applications and patents incorporated herein by reference are expressly incorporated here. The filament 510 may be made of suture, polymer or even metal. The filament 510 may be coupled to the devices 500, 530 at any suitable proximal and distal location. For example, the filament 510 may be attached to the devices 500, 530 at a proximal location with the distal location being at a desirable circumferential or angular distance from the proximal attachment. The filament 510 may be sized to be substantially the same length as the distance between the proximal and distal locations on the elongate element when the elongate element 504 is straightened.

The devices 500, 530, 540 may be used in any manner described or incorporated herein and all such uses are expressly incorporated here. One method of using the device 500 is now described and it is understood that the method applies to devices 500, 530, 540. The device 500 is collapsed into a straightened configuration and advanced through the patient's vascular system to the obstruction. The device 500 may be maintained in the collapsed condition by a delivery catheter or sheath (see FIG. 1) as described above. The distal section 506 is expanded distal to the obstruction so that the distal section 506 may contact and engage the distal portion of the obstruction. Deployment of the distal section 506 may also deploy all or part of the filament 510. The device 500 and catheter are then moved proximally together until the distal section 506 engages the distal portion of the obstruction.

The catheter is then retracted to expose the expandable structures 502. Due to the alternating winding directions of the expanding structures 502, the tip of the catheter does not need to make excessive revolutions around the obstruction. Instead, the tip may remain essentially within a 360 degree range as the device 500 is deployed. In this manner, the structures 502 may help wrap the device 500 around the obstruction without requiring the tip of the catheter to wind completely around the obstruction a number of times as may be necessary with other devices. The structures 502 may also help to push the obstruction away from the vessel wall since the structures 502 may cause the elongate element 504 to turn radially inward to better secure the obstruction.

Figure 52:
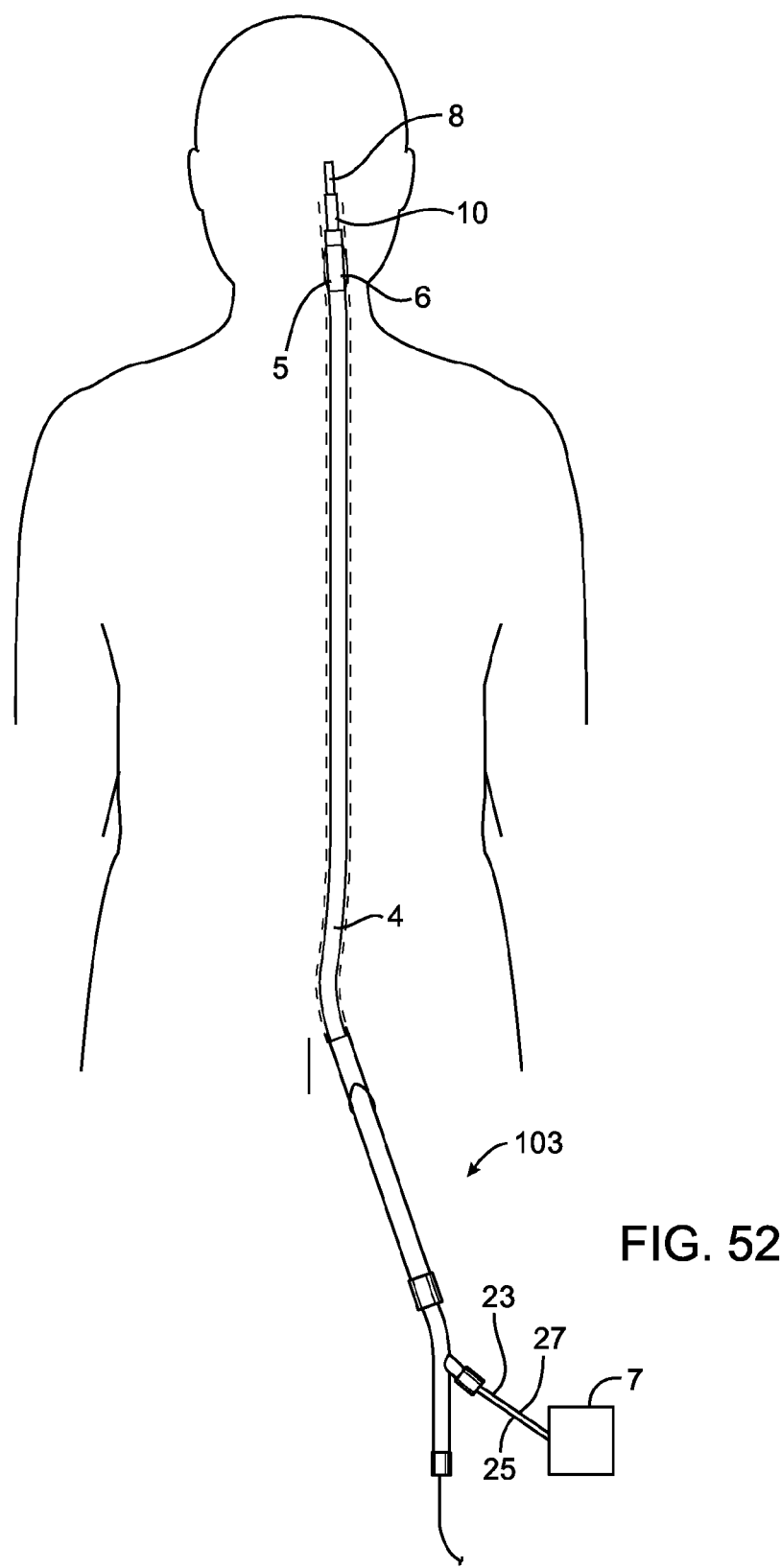
FIG. 52 shows a system for removing an obstruction which includes an obstruction removing element.

Another system 103 for removing an obstruction from a patient is shown in FIG. 52. The guide catheter 4 is advanced to a location proximal to an obstruction. When accessing the cerebral vasculature, for example, the guide catheter 4 is often positioned in the carotid or vertebral artery. Of course, the guide catheter 4 may not be necessary or may be positioned in any other suitable location depending upon the location of the obstruction. The guide catheter 4 preferably has the flow restricting element 6 which restricts or even stops blood flow through the vessel as described below. The flow restricting element 6 is preferably the balloon 5 coupled to the source of inflation fluid 7 which is used to inflate the balloon 5.

An obstruction removing element 100 is advanced through the guide catheter 4 to the obstruction. A microcatheter 10 may also be positioned within the guide catheter 4 to deliver the obstruction removing element 100 further into the vasculature. The obstruction removing element 100 may be advanced by itself through the microcatheter 10 or may be contained within a sheath which is advanced through the microcatheter 10.

Figure 53:
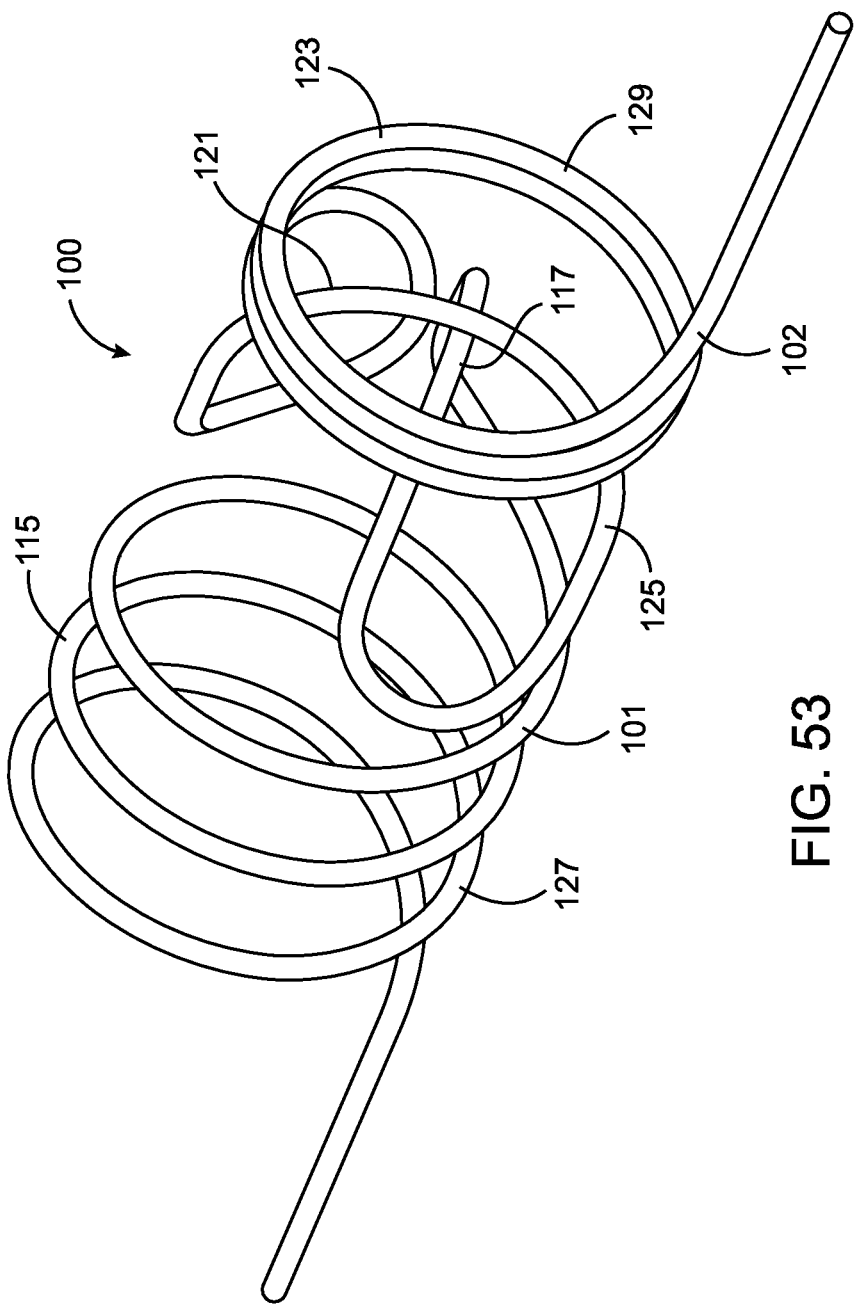
FIG. 53 shows a perspective view of a distal end of an obstruction removing element.
Figure 54:
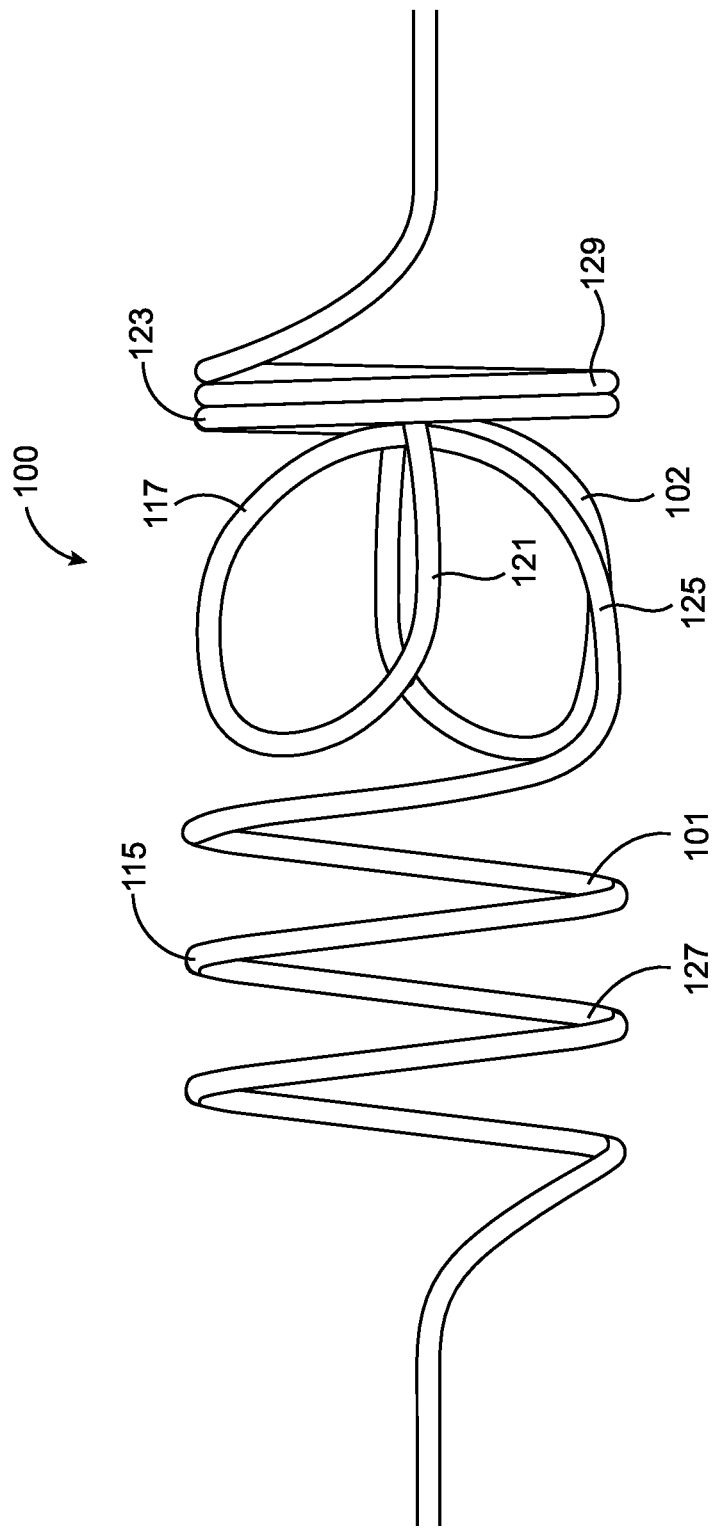
FIG. 54 shows a side view of the obstruction removing element.
Figure 55:
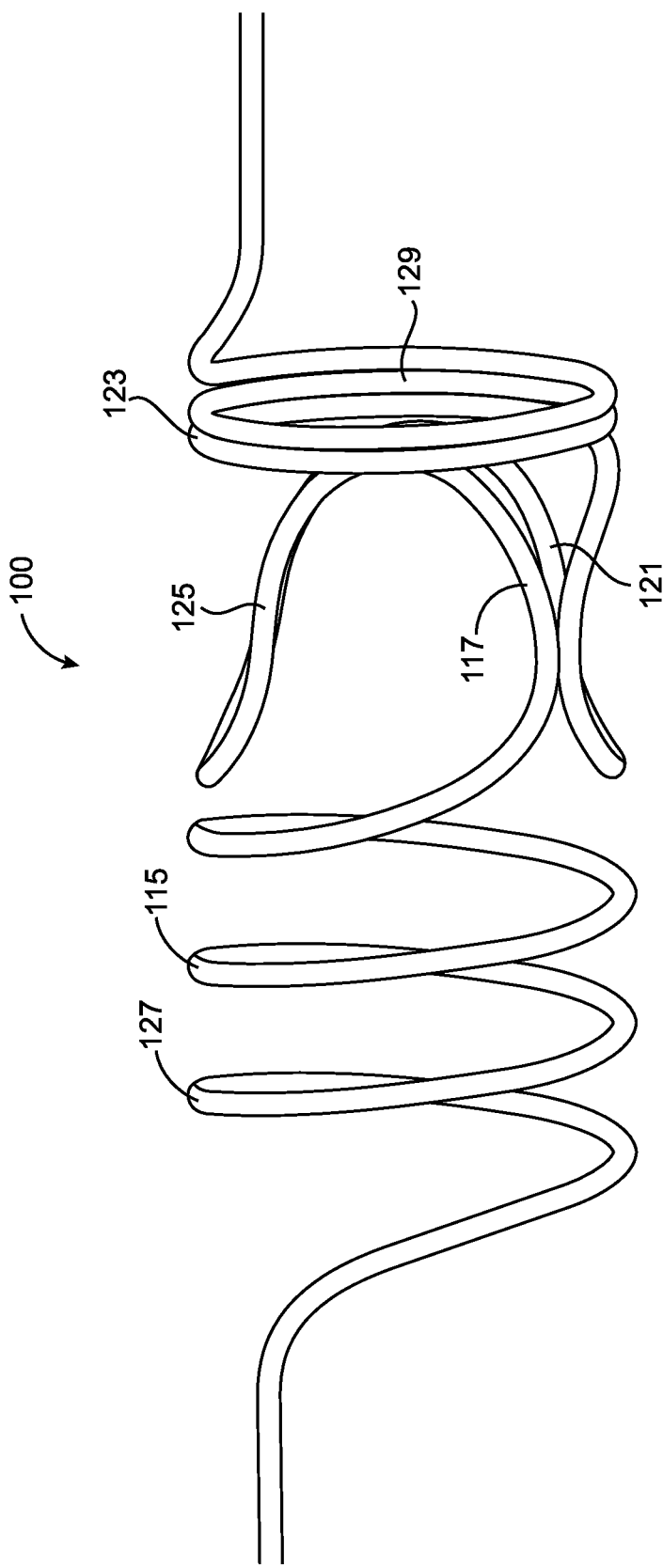
FIG. 55 shows another side view of the obstruction removing element.

The obstruction removing element 100 has an expandable portion 101 which is naturally biased to the expanded position shown in FIGS. 53-55. When the obstruction removing element 100 is contained within the sheath or microcatheter 10, the obstruction removing element 100 is in a relatively straight configuration. The obstruction removing element 100 includes an elongate element 102 which may be any suitable material such as nitinol or any other suitable material.

Referring now to FIGS. 57-62, the elongate element 102 has a shape which is best described by showing the process, system and tools for forming the obstruction removing element 100. The system used to form the obstruction removing element 100 includes a proximal mandrel 104 and a distal mandrel 106 around which the elongate element 102 is wrapped. The proximal and distal mandrels 104, 106 fit together with a pin 108 extending from the proximal mandrel 104 into a hole 110 in the distal mandrel 106.

The elongate element 102 essentially takes a shape of a groove 112 formed in the proximal and distal mandrels 104, 106. Thus, it is understood that when the groove 112 shape or the elongate element 102 shape is described, that the shape of the elongate element 102, or the groove 112, is also being described. Beginning with the groove 112 in the proximal mandrel 104, the groove 112 extends longitudinally until it reaches a coiled section 114 which forms 3¼ turns to form a proximal coiled section 115 in the elongate element 102. The groove 112 then turns distally and forms a first arc 116 over an apex 118 of the proximal mandrel 104. The groove 112 then forms a curved section 109 which winds the element 102 into position to form a second arc 120 over the apex 118. The groove 112 then turns distally before the proximal mandrel 104 is coupled to the distal mandrel 106.

The distal mandrel 106 is then engaged with the proximal mandrel 104 using the pin 108 and hole 110. The groove 112 includes another coiled section 122 having 2¾ turns which forms a distal coiled section 123 in the elongate element 102. Following the coiled section 122, the groove 112 then turns distally and extends longitudinally to complete the desired shape.

Figure 56:
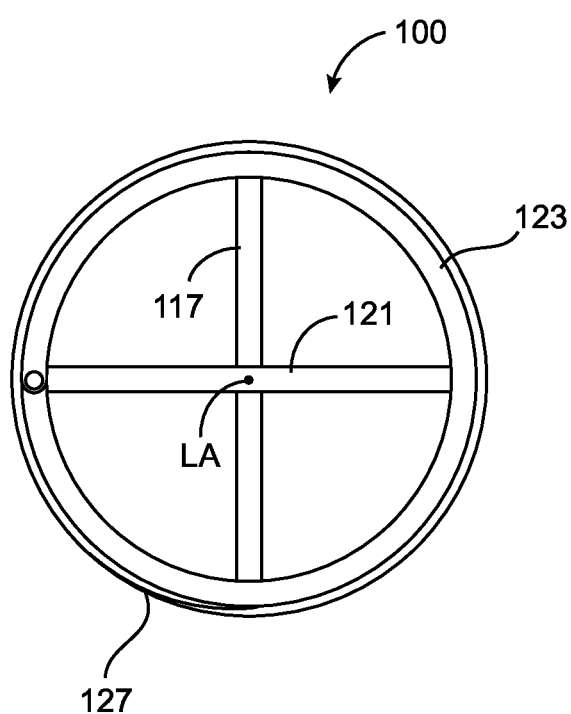
FIG. 56 shows an end view of the obstruction removing element.
Figure 57:
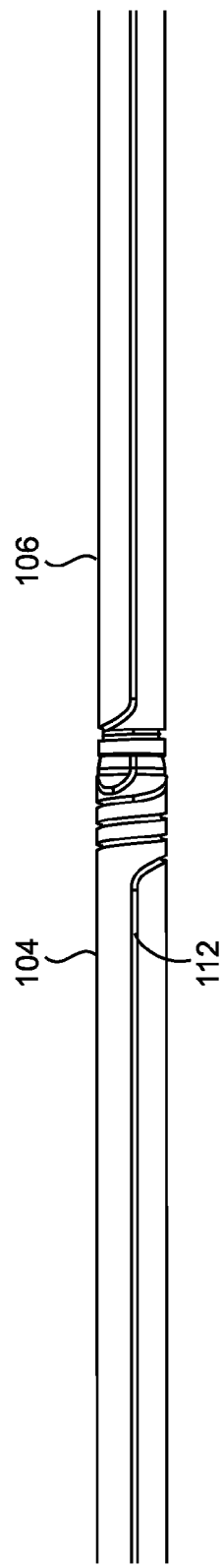
FIG. 57 shows a two-part mandrel used to form the obstruction removing element.
Figure 58:
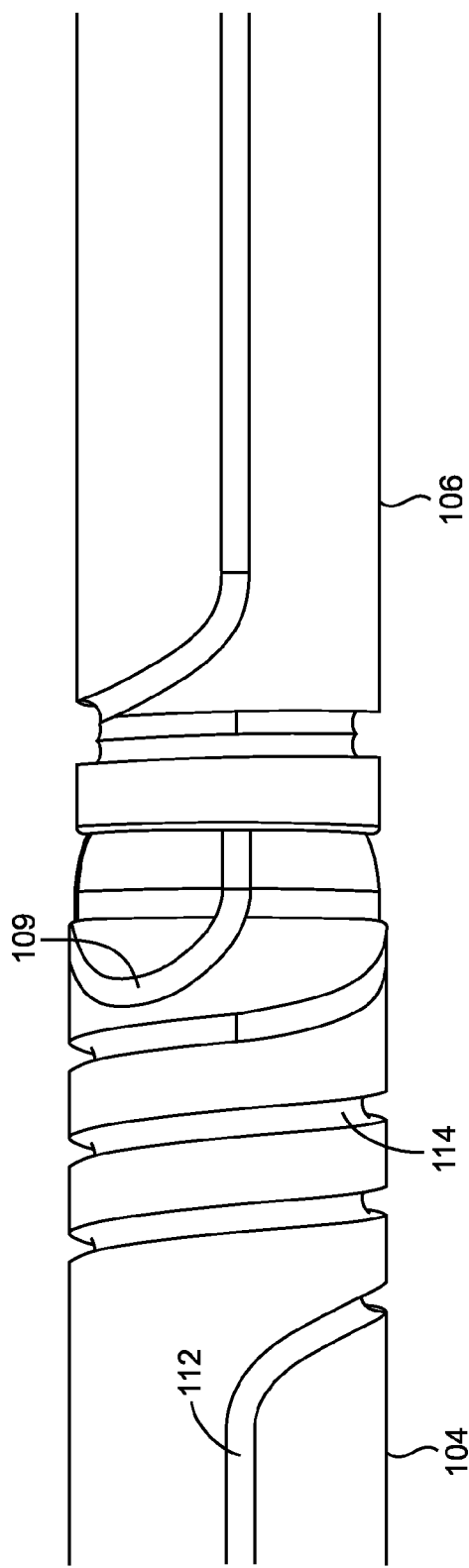
FIG. 58 shows an enlarged portion of the mandrel at the junction of the two parts.
Figure 59:
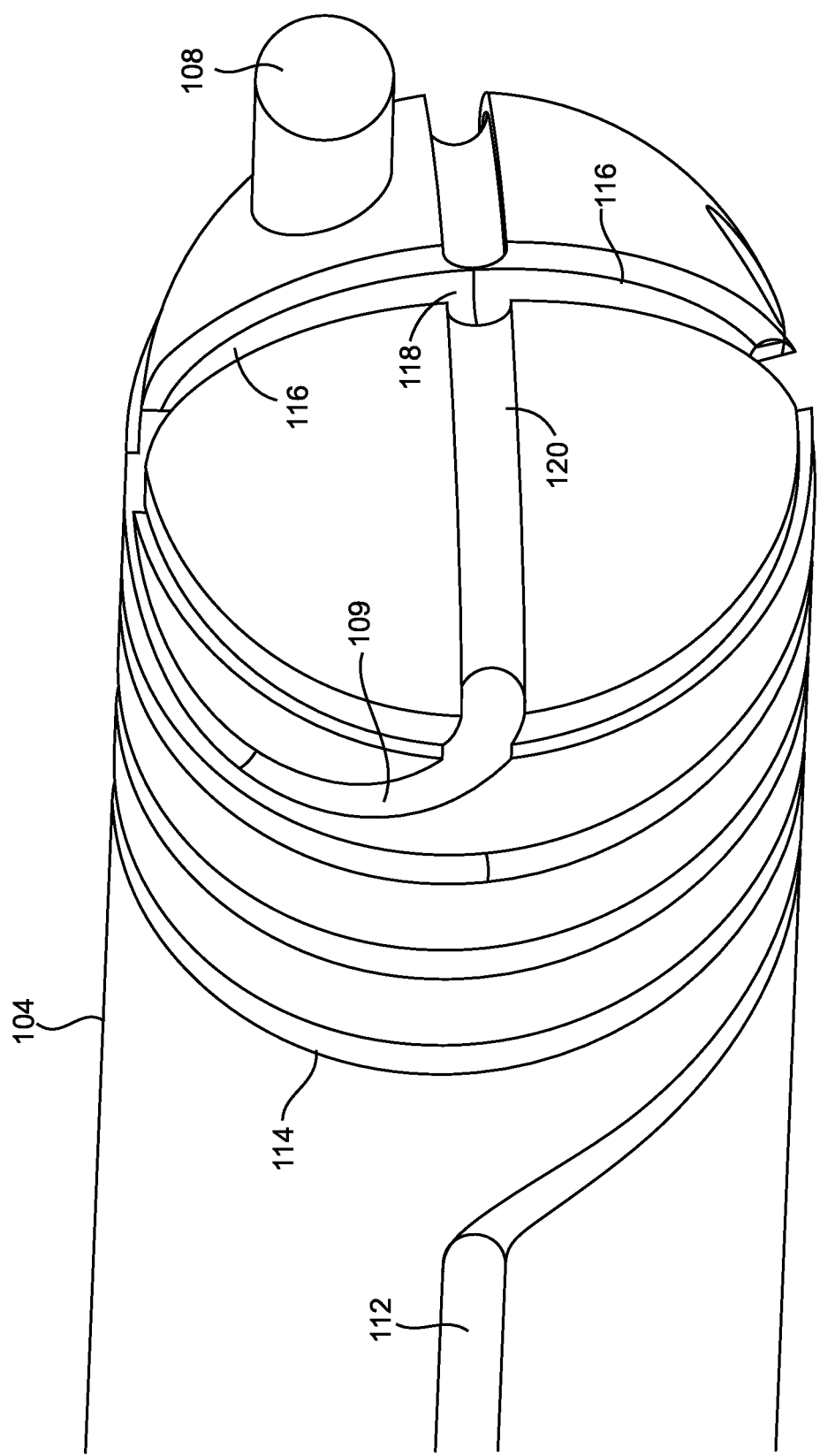
FIG. 59 shows the end of the proximal mandrel.
Figure 60:
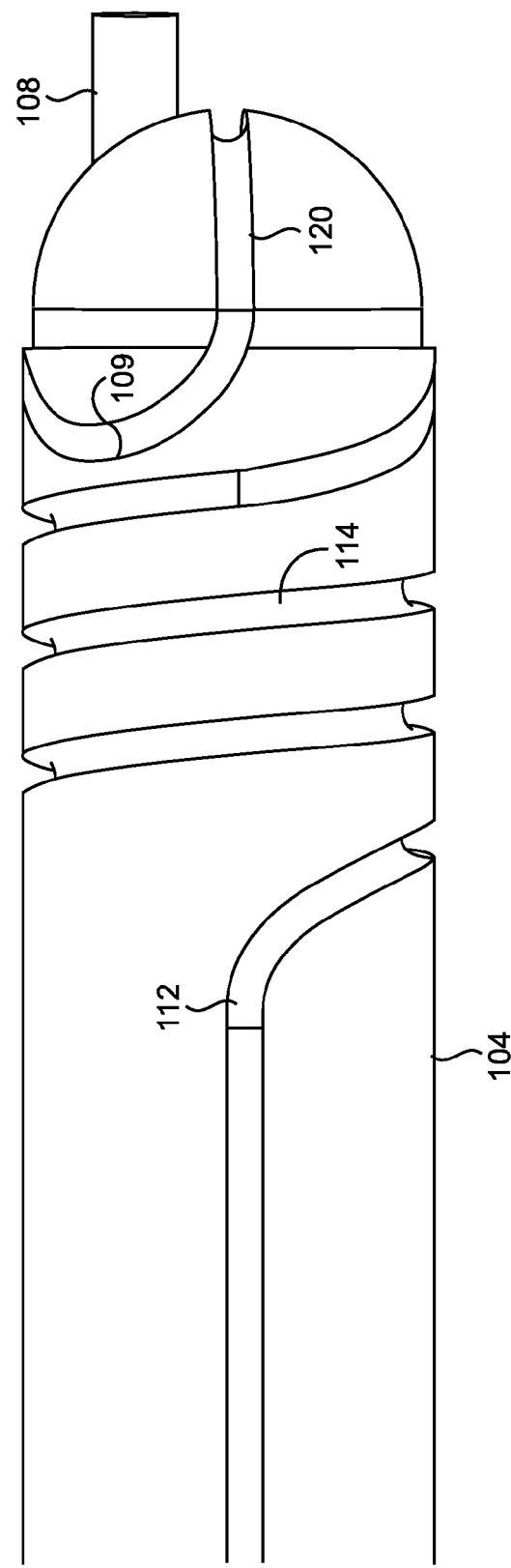
FIG. 60 shows a side view of the proximal mandrel.
Figure 61:
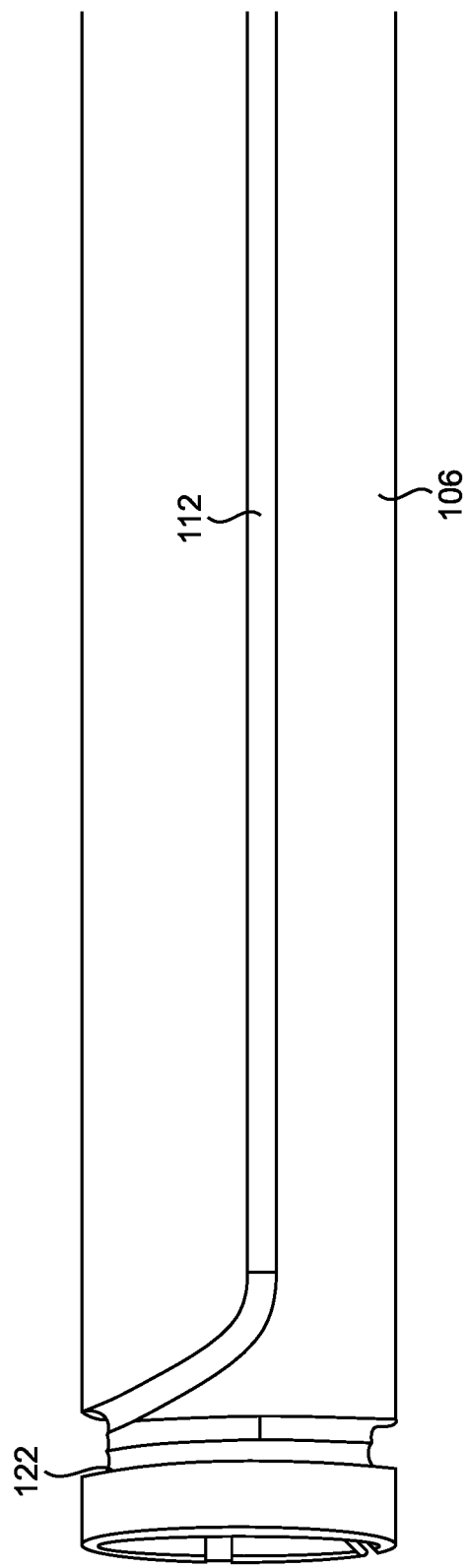
FIG. 61 shows a side view of the distal mandrel.
Figure 62:
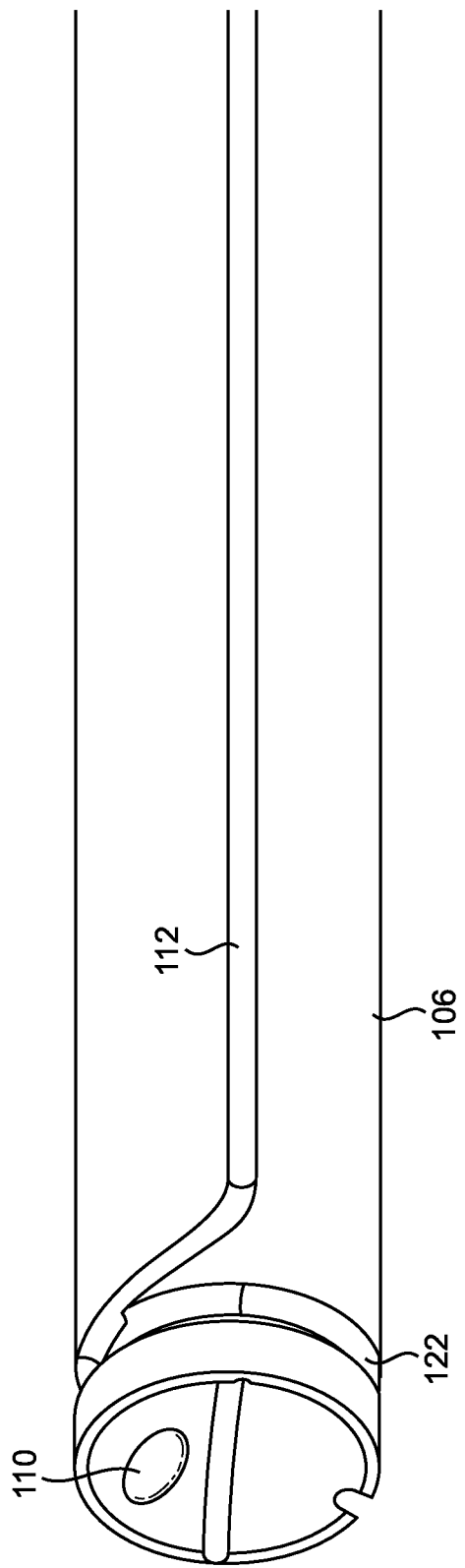
FIG. 62 shows another view of the distal mandrel.

The first and second arcs 116, 120 form crossing sections 117, 121 in the elongate element 102 which intersect the longitudinal axis LA when viewed along the longitudinal axis as shown in FIG. 56. The longitudinal axis is generally defined by the circular shape formed by the proximal or distal coiled sections 115, 123. The crossing sections 117, 121 also change direction relative to the longitudinal axis (proximal vs. distal) when intersecting the longitudinal axis. The crossing sections 117, 121 are positioned along an intermediate section 125 positioned between a proximal section 127, which includes the proximal coiled section 115, and a distal section 129, which includes the distal coiled section 123.

Figure 63:
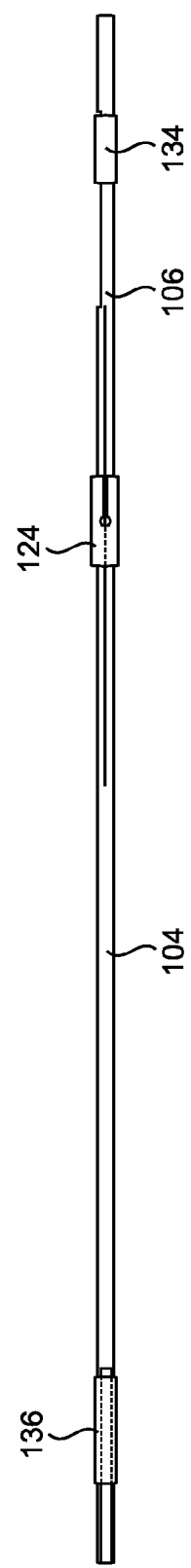
FIG. 63 shows the three sleeves, proximal, keyhole and distal.
Figure 65:
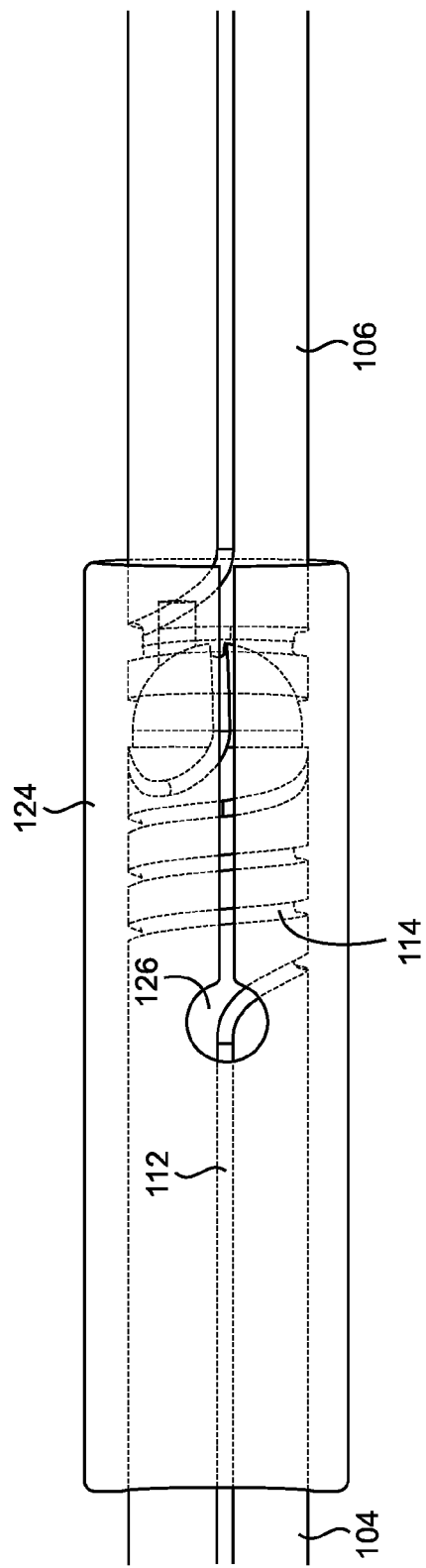
FIG. 65 shows another view of the keyhole sleeve positioned over the mandrel.

Referring to FIGS. 63-65, the elongate element 102 is guided into the groove 112 using a keyhole sleeve 124. The keyhole sleeve 124 extends over the proximal and distal mandrels 104, 106 and has a hole 126 through which the elongate element 102 extends. The sleeve 124 is essentially manipulated in a manner which causes the elongate element 102 to fall into the grooves 112 of the mandrels 104, 106. A slot 128 communicates with the hole 126 and is used to feed the elongate element 102 into and out of the hole 126 and for other maneuvers as described below. The keyhole sleeve 124 also may help to maintain the coaxial position of the mandrels 104, 106 during the heat setting.

The elongate element 102 is wound around the mandrels 104, 106 using the keyhole sleeve 124 in the following manner. First, the keyhole sleeve 124 is placed over the distal end of the proximal mandrel 104 with the elongate element 102 positioned in the hole 126. The keyhole sleeve 124 is then manipulated so that the hole 126 essentially traverses the straight portion of the groove 112 so that the elongate element simply falls within the groove 112 and becomes trapped in the groove 112 by the sleeve 124. The keyhole sleeve 124 is then manipulated so that the hole 126 follows the coiled section 114 of the groove 112 in the proximal mandrel 104 to wind the element 102 around the mandrel 104. At this point, the groove 112 turns distally and forms the first arc 116 over the apex 118 of the proximal mandrel 104. When winding the elongate element 102 to create the first and second arcs 116 120, tension is maintained on the elongate element 102 and the keyhole sleeve 124 is positioned to permit the elongate element 102 to escape through the end of the slot 128. The element 102, which is now free from the hole 126 and slot 128 of the sleeve 124, is wrapped over the mandrel 104. The sleeve 124 is then rotated 180 degrees to align the slot 128 with the end of the arc 116, 120 to feed the elongate element 102 back into the keyhole sleeve 124. The distal mandrel 106 is then engaged with the proximal mandrel using the pin 108 and hole 110 engagement. The keyhole sleeve 124 is manipulated in substantially the same manner to cause the elongate element 102 to fall into the coiled section 122 of the groove 112 in the distal mandrel 106. Once the elongate element 102 is properly positioned in the groove 112, a distal sleeve 134 and/or proximal sleeve 136 may be advanced over the proximal or distal mandrels 104, 106 to help hold the elongate element 102 in place during heat forming.

Use of the obstruction removing element 100 is now described. The guide catheter 4 is introduced into the patient and delivered proximal to the target vessel such as to the carotid or vertebral artery. The microcatheter 10 is then advanced through the guide catheter 4 further into the vasculature to a position proximal to, within or distal to the obstruction. The obstruction removing element 100 is then advanced through the microcatheter 10 either by itself or pre-loaded within the sheath 12. The obstruction removing element 100 is then advanced to the obstruction. Before advancing the obstruction removing element 100 further, the flow restricting element 6 on the guide catheter 4 is expanded to reduce and even stop flow through the vessel. Stopping flow in the vessel may help prevent the obstruction, or any parts thereof, from migrating downstream. Reducing flow through the vessel may also reduce the likelihood that the obstruction is disrupted by a combination of flow and the obstruction removal device 8.

The microcatheter 10 is then advanced into the obstruction and the obstruction removing element 100 is then positioned so that part of the obstruction removing element 100 is within the obstruction while a portion, such as the distal coil section 123, are positioned distal to the obstruction. The obstruction removing element 100 is then moved out of the microcatheter 10 to permit the obstruction removing element 100 to expand by withdrawing the microcatheter and/or advancing the obstruction removing element 100. The obstruction removing element 100 is then manipulated to engage and dislodge the obstruction. The obstruction may then be removed by applying suction to the guide catheter 4 to hold and/or contain the obstruction for removal or with use of another suitable device.

Figure 66:
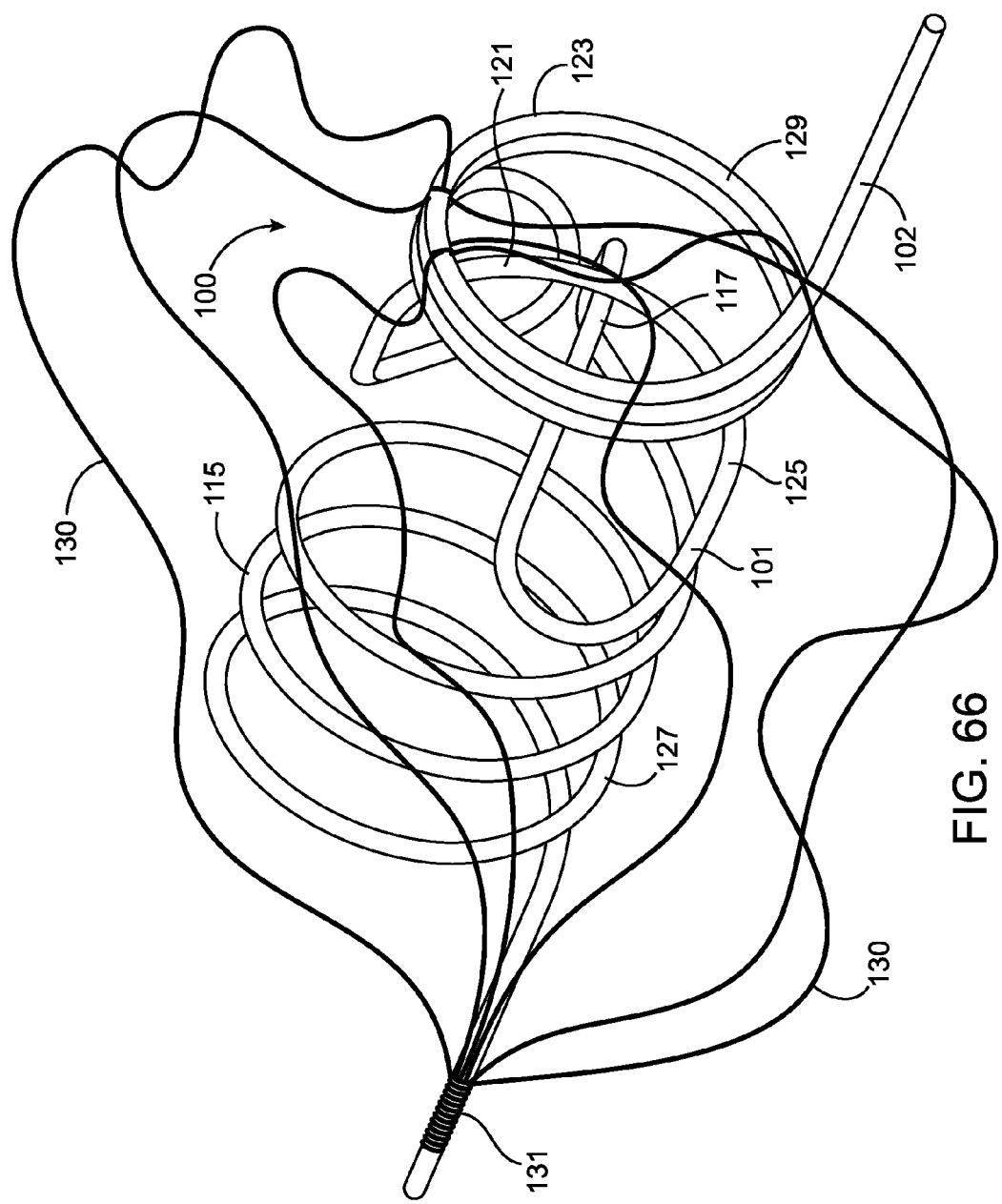
FIG. 66 shows a number of strands coupled to the obstruction removing element.
Figure 67:
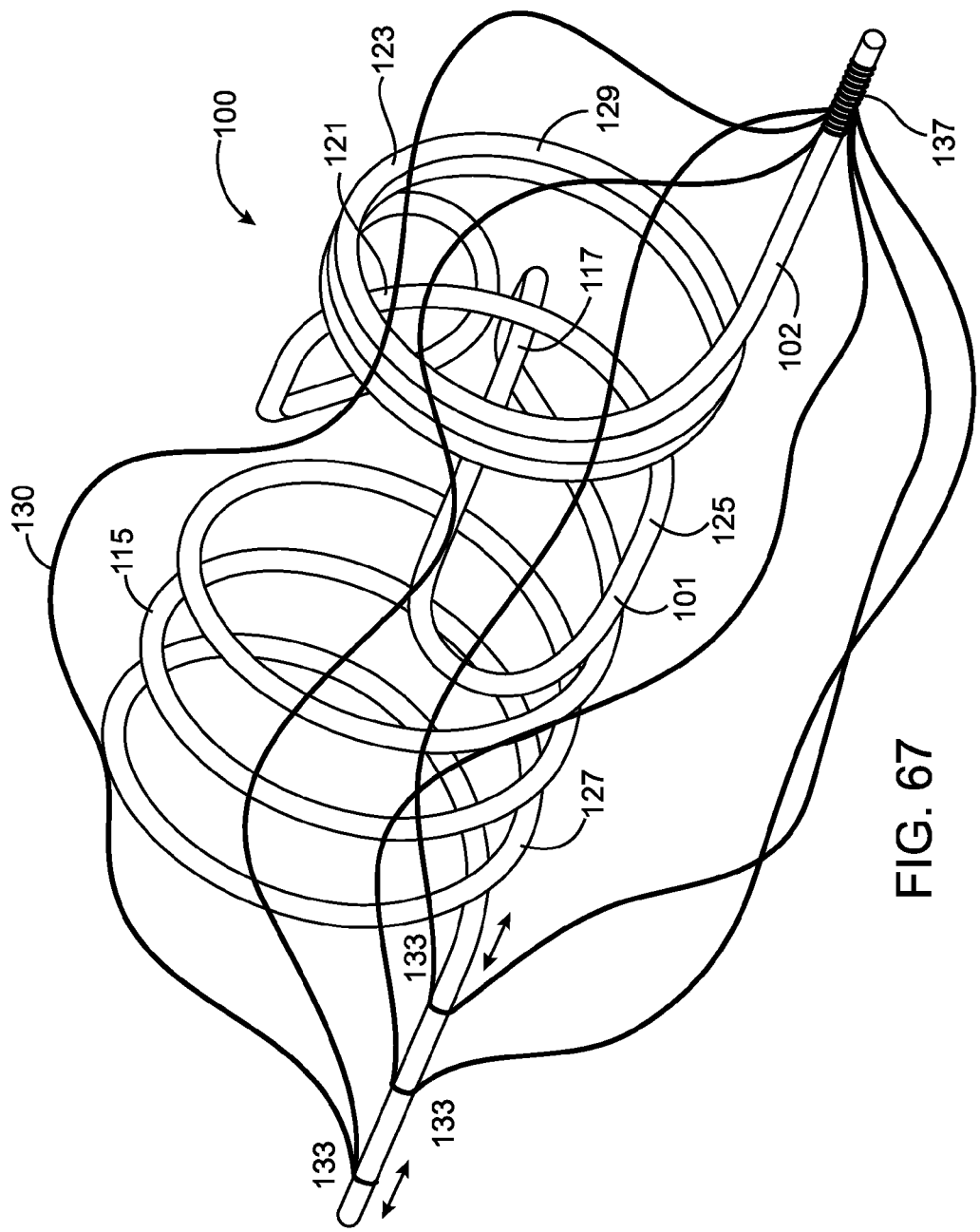
FIG. 67 shows another embodiment with a number of strands coupled to the obstruction removing element.

Referring now to FIGS. 66 and 67, the obstruction removing element 100 is shown with a number of strands 130 similar to the strand 906 and filaments 510 described above and the discussion of the strands 906 and filaments 510 are equally applicable here. The strands 130 extend alongside the element 100 when the element 100 is collapsed similar to the embodiment of FIG. 2. The strands 130 may be coupled to the element 100 at a proximal location and a distal location. The proximal location may be coupled to the element by holding the strands 130 with a filament 131 wrapped around the element 101 as shown in FIG. 66. The distal end of the strands 130 may be wrapped or otherwise coupled to the distal coils 123. Referring to FIG. 67, the proximal end 133 of the strands 130 may also be slidable on the element 100 so that the position of the proximal end 133 may depend on the manner in which the element 100 expands within the vessel. The distal end 135 of the strands 130 may be coupled to the element 100 by holding the strands 130 with a filament 137 wrapped around the element 100.

When the element 100 expands within the vessel, the element 100 may also expand with the element 100 temporarily undergoing a rotary or helical motion so that the rotary or helical motion causes the strand to engage the element 100 in a manner dependent upon the expansion of the element 100. The element 100 of FIGS. 68 and 69 may also simply be manipulated to cause the strands 130 to become entangled with the element 100. For example, the element 100 may be pulled or otherwise manipulated so that the strands 130 engage the element at the plurality of locations thereby reducing distortion of the element 100.

While the above is a description of the preferred embodiments of the invention, various alternatives, substitutions and modifications may be made without departing from the scope thereof, which is defined by the following claims. Thus, the preferred embodiments should not be taken as limiting the scope of the invention. For example, although all of the obstruction removal devices described herein are self-expanding structures, the obstruction removal devices may also have actuating mechanisms for moving the engaging element between the expanded and collapsed positions. Furthermore, the present invention is directed to a number of separate inventions and each of these inventions may be claimed independently of one another. Each feature, aspect and advantage of the invention may be claimed independent of one another without departing from the scope of the invention.

What is claimed is:

1. A method for removing an obstruction from a cerebral vessel, comprising the steps of:
    providing an obstruction removing device having an elongate element, the elongate element being movable from a collapsed position to an expanded position and being naturally biased toward the expanded position, the elongate element having a proximal section, a distal section and an intermediate section, the intermediate section being positioned between the distal and proximal sections, at least one of the proximal and distal sections forming at least two loops having a longitudinal axis, the intermediate section having a first crossing portion which intersects the longitudinal axis and a second crossing portion which also intersects the longitudinal axis, the at least two loops forming a circle when viewed along the longitudinal axis, the first and second crossing sections extending diametrically across the circle when viewed along the longitudinal axis;
    introducing the obstruction removing device into a patient with the elongate element being in the collapsed position;
    expanding the elongate element after the introducing step;
    engaging an obstruction with the elongate element; and
    removing the obstruction with the elongate element.

2. The method of claim 1, wherein:
the providing step is carried out with the proximal section and the distal section both having at least two loops.

3. The method of claim 1, wherein:
the providing step is carried out with the first and second crossing sections being substantially perpendicular to one another when viewed along the longitudinal axis.

4. The method of claim 1, wherein:
the providing step is carried out with a strand extending alongside the elongate element when in the collapsed position.

5. The method of claim 4, wherein:
the expanding step is carried out with the strand extending between the proximal and distal sections dependent upon the permitted expansion of the elongate element.

6. The method of claim 4, wherein:
the providing step is carried out with the strand being coupled to the elongate element at a proximal location and a distal location, wherein at least one of the proximal and distal locations is slidable relative to the elongate element.

7. The method of claim 4, wherein:
the expanding step is carried out with the elongate element expanding in a helical motion so that the helical motion causes the strand to engage the elongate element at a location dependent upon expansion of the element.

8. The method of claim 4, wherein:
the providing step is carried out with a plurality of strands coupled to the elongate element.

* * * * *